US012597510B2

(12) United States Patent
Rodts et al.

(10) Patent No.: US 12,597,510 B2
(45) Date of Patent: Apr. 7, 2026

(54) TECHNOLOGIES FOR MEDICAL DEVICE USAGE TRACKING AND ANALYSIS

(71) Applicant: DePuy Synthes Products, Inc., Raynham, MA (US)

(72) Inventors: Timothy W. Rodts, Westerville, OH (US); Julio Guerrero, Cambridge, MA (US); Stephen A. Kramer, Buzzards Bay, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 316 days.

(21) Appl. No.: 18/105,015

(22) Filed: Feb. 2, 2023

(65) Prior Publication Data

US 2023/0274823 A1     Aug. 31, 2023

Related U.S. Application Data

(60) Provisional application No. 63/314,449, filed on Feb. 27, 2022.

(51) Int. Cl.
*G16H 40/20*          (2018.01)
*G06V 10/12*          (2022.01)
             (Continued)

(52) U.S. Cl.
CPC ............. *G16H 40/20* (2018.01); *G06V 10/12* (2022.01); *G06V 10/95* (2022.01); *G06V 20/52* (2022.01);
             (Continued)

(58) Field of Classification Search
CPC ........ G16H 40/20; G06V 10/12; G06V 20/70; G06V 20/52; G06V 10/95; G06V 2201/034
See application file for complete search history.

(56) References Cited

U.S. PATENT DOCUMENTS 7,118,029 B2   10/2006  Nycz et al.
7,362,228 B2    4/2008  Nycz et al.
              (Continued)

OTHER PUBLICATIONS

Nosrati, R., Emaminejad, N., Ganapathi, S et al. Advancing industrial inspection with an automated computer vision solution for orthopedic surgical tray inspection. Sci Rep 15, 7867 (2025). (Year: 2025).*
              (Continued)

*Primary Examiner* — Matthew L Hamilton
(74) *Attorney, Agent, or Firm* — Barnes & Thornburg LLP

(57) ABSTRACT

A system for medical device usage monitoring includes one or more capture devices, one or more base station devices, and an analytics server. The capture devices each capture image data indicative of a monitored location at a timestamp in an operating room and transmit the image data to a base station device. Each base station device recognizes medical devices in the image capture data with a trained machine learning model and transmits recognition data to the analytics server. The analytics server generates medical device usage data over time based on the recognition data. The analytics server may infer usage based on the recognition data. The analytics server may analyze the medical device usage data and generate analytical usage data. Methods associated with the system are also disclosed.

11 Claims, 15 Drawing Sheets

(51) Int. Cl.

| | |
|---|---|
| *G06V 10/94* | (2022.01) |
| *G06V 20/52* | (2022.01) |
| *G06V 20/70* | (2022.01) |

(52) U.S. Cl.

CPC ........ *G06V 20/70* (2022.01); *G06V 2201/034* (2022.01)

(56) References Cited

U.S. PATENT DOCUMENTS

| | | | |
|---|---|---|---|
| 10,504,623 | B2 | 12/2019 | Woods et al. |
| 10,758,309 | B1 * | 9/2020 | Chow ..................... G06F 18/21 |
| 2006/0043179 | A1 | 3/2006 | Nycz et al. |
| 2006/0244593 | A1 | 11/2006 | Nycz et al. |
| 2008/0150722 | A1 | 6/2008 | Jackson |
| 2009/0272806 | A1 | 11/2009 | Kemp et al. |
| 2009/0317002 | A1 | 12/2009 | Dein |
| 2011/0036738 | A1 | 2/2011 | Hiltl |
| 2013/0113929 | A1 * | 5/2013 | DeLand ................. A61B 90/90 382/103 |
| 2014/0152238 | A1 | 6/2014 | Racent et al. |
| 2015/0190202 | A1 | 7/2015 | Weinert et al. |
| 2017/0098049 | A1 * | 4/2017 | Sweeney ............ G06Q 10/0875 |
| 2017/0363554 | A1 | 12/2017 | Freeman et al. |
| 2018/0204323 | A1 | 7/2018 | Sayani et al. |
| 2018/0214243 | A1 | 8/2018 | Weinert et al. |
| 2019/0053814 | A1 * | 2/2019 | Hoogland .......... A61B 17/1757 |
| 2019/0090954 | A1 | 3/2019 | Kotian et al. |
| 2020/0193241 | A1 * | 6/2020 | Katayama .............. A61B 34/20 |
| 2022/0292815 | A1 * | 9/2022 | Donnelly ............. G06V 10/761 |

OTHER PUBLICATIONS

Cottrill, "Post-Pandemic Supply Chains: A Prognosis from Johnson & Johnson," Mar. 17, 2021, 5 pages.

Smith, "Framework for Establishing Asset Visibility and Traceability of Medical Devices," "Mass. Inst. Tech., May 2020, 115 pages."

Oporto et al., "Data Aggregation for Data Analytics in Medical Device Supply Chains," Mass. Inst. Tech., May 2020, 37 pages.

Capra et al., "Implementing a perioperative efficiency initiative for orthopedic surgery instrumentation at an academic center: A comparative before-and-after study," Medicine, 98:7(e14338), 2019, 7 pages.

Peter F. Hu et al., Advanced Visualization Platform for Surgical Operating Room Coordination: Distributed Video Board System, Technology Research and Development; Surgical Innovation ResearchGate, Jun. 2006, 8 pages, vol. 13 No. 2, Sage Publications.

Imran Ahmed et al., A Framework for Pandemic Prediction Using Big Data Analytics, Elsevier Public Health Emergency Collection, Jul. 2021, 32 pages, Elsevier Inc.

* cited by examiner

Figure 6:
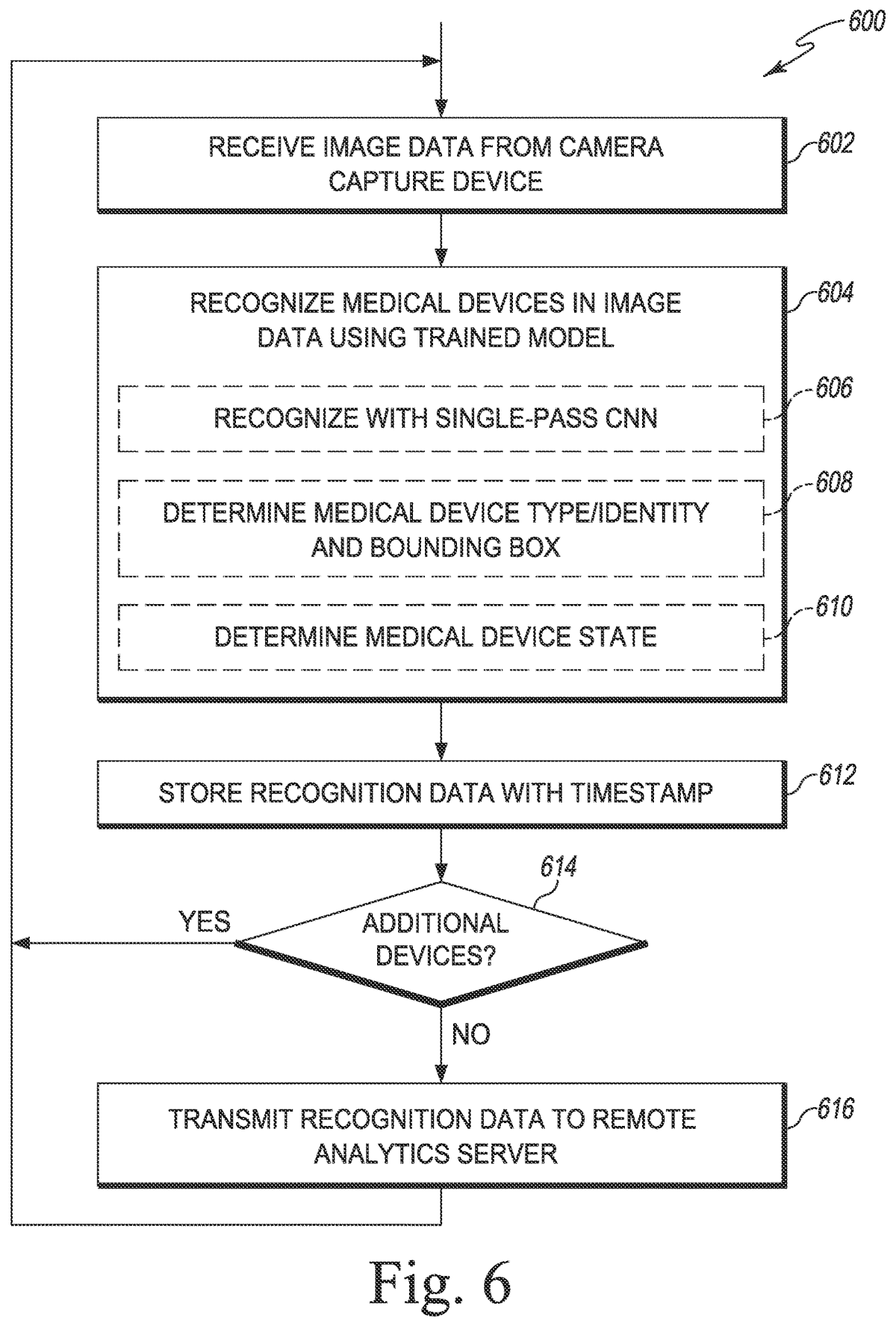

_600_

```
┌──────────────────────────────────────────┐
│     RECEIVE IMAGE DATA FROM CAMERA        │── 602
│            CAPTURE DEVICE                 │
└──────────────────────────────────────────┘
                    │
                    ▼
┌──────────────────────────────────────────┐
│    RECOGNIZE MEDICAL DEVICES IN IMAGE     │── 604
│       DATA USING TRAINED MODEL            │
│  ┌────────────────────────────────────┐  │
│  │   RECOGNIZE WITH SINGLE-PASS CNN    │  │── 606
│  └────────────────────────────────────┘  │
│  ┌────────────────────────────────────┐  │
│  │ DETERMINE MEDICAL DEVICE TYPE/      │  │── 608
│  │ IDENTITY AND BOUNDING BOX           │  │
│  └────────────────────────────────────┘  │
│  ┌────────────────────────────────────┐  │
│  │  DETERMINE MEDICAL DEVICE STATE     │  │── 610
│  └────────────────────────────────────┘  │
└──────────────────────────────────────────┘
                    │
                    ▼
┌──────────────────────────────────────────┐
│   STORE RECOGNITION DATA WITH TIMESTAMP   │── 612
└──────────────────────────────────────────┘
                    │
                    ▼
               ╱─────────╲
      YES      ╱  ADDITIONAL ╲       _614_
     ◄────────   DEVICES?    
               ╲           ╱
                ╲─────────╱
                    │ NO
                    ▼
┌──────────────────────────────────────────┐
│  TRANSMIT RECOGNITION DATA TO REMOTE      │── 616
│            ANALYTICS SERVER               │
└──────────────────────────────────────────┘
```

Figure 7:
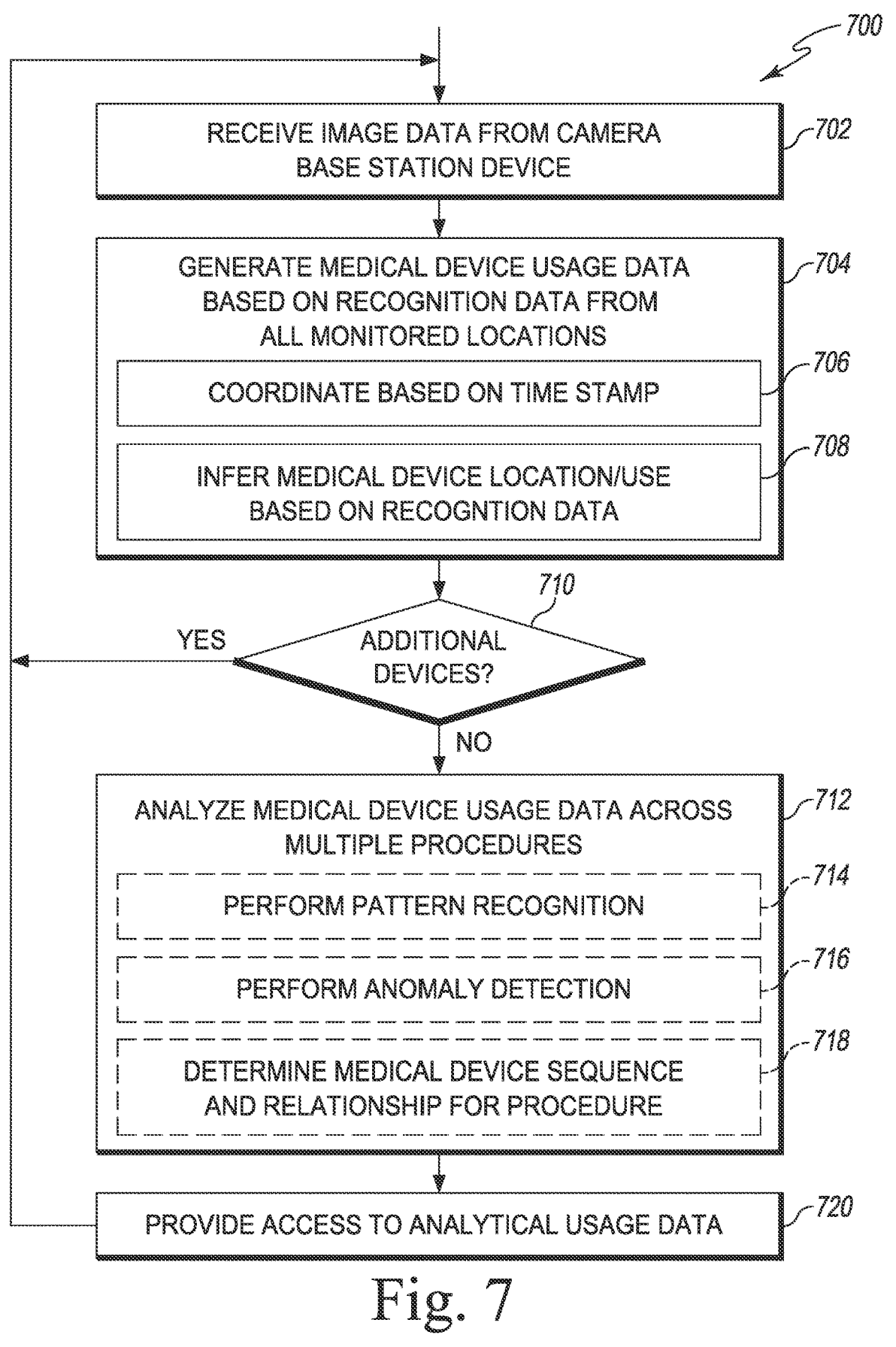

RECEIVE IMAGE DATA FROM CAMERA
BASE STATION DEVICE — *702*

GENERATE MEDICAL DEVICE USAGE DATA
BASED ON RECOGNITION DATA FROM
ALL MONITORED LOCATIONS — *704*

COORDINATE BASED ON TIME STAMP — *706*

INFER MEDICAL DEVICE LOCATION/USE
BASED ON RECOGNTION DATA — *708*

*710*

YES     ADDITIONAL
DEVICES?

NO

ANALYZE MEDICAL DEVICE USAGE DATA ACROSS
MULTIPLE PROCEDURES — *712*

PERFORM PATTERN RECOGNITION — *714*

PERFORM ANOMALY DETECTION — *716*

DETERMINE MEDICAL DEVICE SEQUENCE
AND RELATIONSHIP FOR PROCEDURE — *718*

PROVIDE ACCESS TO ANALYTICAL USAGE DATA — *720*

Figure 8:
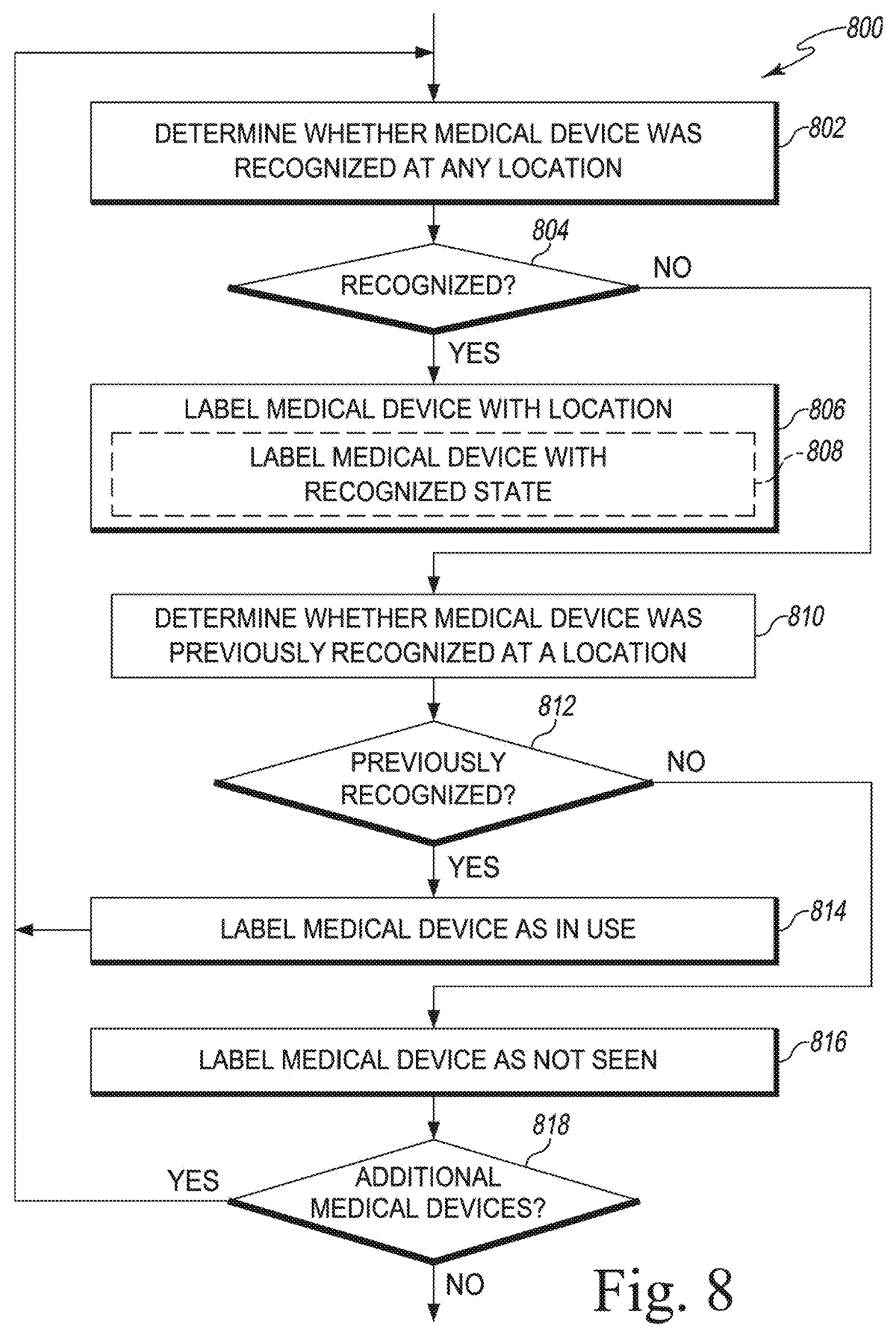

DETERMINE WHETHER MEDICAL DEVICE WAS RECOGNIZED AT ANY LOCATION *802*

RECOGNIZED? *804*

NO

YES

LABEL MEDICAL DEVICE WITH LOCATION *806*

LABEL MEDICAL DEVICE WITH RECOGNIZED STATE *808*

DETERMINE WHETHER MEDICAL DEVICE WAS PREVIOUSLY RECOGNIZED AT A LOCATION *810*

PREVIOUSLY RECOGNIZED? *812*

NO

YES

LABEL MEDICAL DEVICE AS IN USE *814*

LABEL MEDICAL DEVICE AS NOT SEEN *816*

YES

ADDITIONAL MEDICAL DEVICES? *818*

| TIME | TABLE1 | | | | | | | | TABLE2 | | | | | | | |
|---|---|---|---|---|---|---|---|---|---|---|---|---|---|---|---|---|
| | T0 | T1 | T2 | T3 | T4 | T5 | T6 | T7 | T0 | T1 | T2 | T3 | T4 | T5 | T6 | T7 |
| 0 | 0 | 0 | 0 | 0 | 0 | 0 | 0 | 0 | 0 | 0 | 0 | 0 | 0 | 0 | 0 | 0 |
| 1 | 1 | 0 | 0 | 0 | 0 | 0 | 0 | 0 | 0 | 0 | 0 | 0 | 0 | 0 | 0 | 0 |
| 2 | 1 | 0 | 0 | 0 | 0 | 0 | 0 | 0 | 0 | 0 | 0 | 0 | 0 | 0 | 0 | 0 |
| 3 | 0 | 1 | 1 | 1 | 0 | 0 | 0 | 0 | 0 | 0 | 0 | 0 | 0 | 0 | 0 | 0 |
| 4 | 0 | 1 | 1 | 0 | 0 | 0 | 0 | 0 | 0 | 0 | 0 | 0 | 0 | 0 | 0 | 0 |
| 5 | 0 | 1 | 1 | 0 | 0 | 0 | 0 | 0 | 0 | 0 | 0 | 0 | 0 | 0 | 0 | 0 |
| 6 | 0 | 1 | 1 | 0 | 0 | 0 | 0 | 0 | 0 | 0 | 0 | 1 | 0 | 0 | 0 | 0 |
| 7 | 0 | 1 | 1 | 0 | 1 | 0 | 0 | 0 | 0 | 0 | 0 | 1 | 0 | 0 | 0 | 0 |
| 8 | 0 | 1 | 1 | 0 | 1 | 1 | 0 | 0 | 0 | 0 | 0 | 1 | 0 | 0 | 0 | 0 |
| 9 | 0 | 1 | 1 | 0 | 1 | 1 | 0 | 0 | 0 | 0 | 0 | 1 | 0 | 0 | 0 | 0 |
| 10 | 0 | 1 | 1 | 0 | 0 | 0 | 0 | 0 | 0 | 0 | 0 | 1 | 0 | 0 | 0 | 0 |
| 11 | 0 | 1 | 1 | 0 | 0 | 0 | 0 | 0 | 0 | 0 | 0 | 1 | 0 | 0 | 0 | 0 |
| 12 | 0 | 1 | 1 | 0 | 0 | 0 | 0 | 0 | 0 | 0 | 0 | 1 | 0 | 0 | 0 | 0 |
| 13 | 0 | 1 | 1 | 0 | 0 | 0 | 1 | 0 | 0 | 0 | 0 | 1 | 1 | 0 | 0 | 0 |
| 14 | 0 | 1 | 1 | 0 | 0 | 0 | 1 | 0 | 0 | 0 | 0 | 1 | 1 | 0 | 0 | 0 |
| 15 | 0 | 1 | 1 | 0 | 0 | 0 | 1 | 0 | 0 | 0 | 0 | 1 | 1 | 1 | 0 | 0 |
| 16 | 0 | 1 | 1 | 0 | 0 | 0 | 0 | 0 | 0 | 0 | 0 | 1 | 1 | 1 | 0 | 0 |
| 17 | 0 | 1 | 1 | 0 | 0 | 0 | 0 | 0 | 0 | 0 | 0 | 1 | 1 | 1 | 0 | 0 |
| 18 | 0 | 1 | 1 | 0 | 0 | 0 | 0 | 0 | 0 | 0 | 0 | 1 | 1 | 1 | 0 | 0 |
| 19 | 0 | 1 | 1 | 0 | 0 | 0 | 0 | 0 | 0 | 0 | 0 | 1 | 1 | 1 | 1 | 0 |

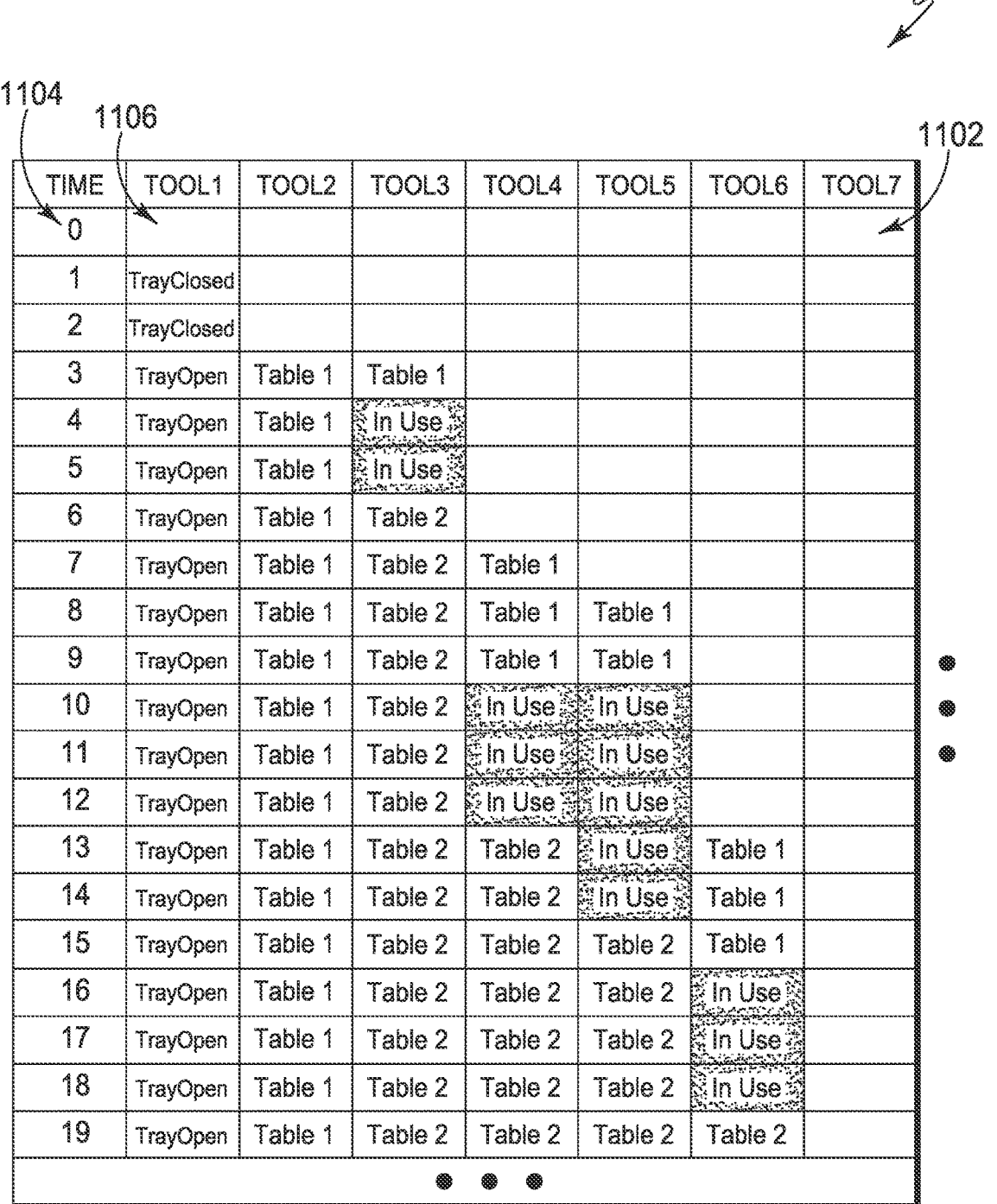

| TIME | TOOL1 | TOOL2 | TOOL3 | TOOL4 | TOOL5 | TOOL6 | TOOL7 |
|------|-------|-------|-------|-------|-------|-------|-------|
| 0 | | | | | | | |
| 1 | TrayClosed | | | | | | |
| 2 | TrayClosed | | | | | | |
| 3 | TrayOpen | Table 1 | Table 1 | | | | |
| 4 | TrayOpen | Table 1 | In Use | | | | |
| 5 | TrayOpen | Table 1 | In Use | | | | |
| 6 | TrayOpen | Table 1 | Table 2 | | | | |
| 7 | TrayOpen | Table 1 | Table 2 | Table 1 | | | |
| 8 | TrayOpen | Table 1 | Table 2 | Table 1 | Table 1 | | |
| 9 | TrayOpen | Table 1 | Table 2 | Table 1 | Table 1 | | |
| 10 | TrayOpen | Table 1 | Table 2 | In Use | In Use | | |
| 11 | TrayOpen | Table 1 | Table 2 | In Use | In Use | | |
| 12 | TrayOpen | Table 1 | Table 2 | In Use | In Use | | |
| 13 | TrayOpen | Table 1 | Table 2 | Table 2 | In Use | Table 1 | |
| 14 | TrayOpen | Table 1 | Table 2 | Table 2 | In Use | Table 1 | |
| 15 | TrayOpen | Table 1 | Table 2 | Table 2 | Table 2 | Table 1 | |
| 16 | TrayOpen | Table 1 | Table 2 | Table 2 | Table 2 | In Use | |
| 17 | TrayOpen | Table 1 | Table 2 | Table 2 | Table 2 | In Use | |
| 18 | TrayOpen | Table 1 | Table 2 | Table 2 | Table 2 | In Use | |
| 19 | TrayOpen | Table 1 | Table 2 | Table 2 | Table 2 | Table 2 | |

Fig. 11

TECHNOLOGIES FOR MEDICAL DEVICE USAGE TRACKING AND ANALYSIS

CROSS-REFERENCE TO RELATED APPLICATIONS

This application claims the benefit of and priority to U.S. Patent Application No. 63/314,449, entitled "TECHNOLOGIES FOR MEDICAL DEVICE USAGE TRACKING AND ANALYSIS," which was filed on Feb. 27, 2022, and which is incorporated herein by reference in its entirety.

TECHNICAL FIELD

The present disclosure relates generally to asset tracking and analysis systems, and more particularly to systems for tracking use of medical devices during a surgical procedure.

BACKGROUND

Joint arthroplasty is a well-known surgical procedure by which a diseased and/or damaged natural joint is replaced by a prosthetic joint. For example, in a total hip arthroplasty surgical procedure, a patient's natural hip joint is partially or totally replaced by a prosthetic hip joint or hip prosthesis. As another example, in a total knee arthroplasty surgical procedure, a patient's natural knee joint is partially or totally replaced by a prosthetic knee joint or knee prosthesis.

During a surgical procedure, the surgeon typically uses a variety of different medical devices. For example, during an orthopaedic surgical procedure, the surgeon may use medical devices including orthopaedic surgical instruments such as, for example, surgical reamers, broaches, impactors and impaction handles, prosthetic trials, trial liners, drill guides, cutting blocks, surgical saws, ligament balancers, and other medical devices to prepare the patient's bones to receive the prosthesis. Many medical devices are reusable, durable goods and thus may have long service lives. Reusable medical devices are typically sterilized between uses using an autoclave or other sterilizer.

Certain systems may track the position and/or identity of medical devices used during a surgical procedure. Many traditional tracking systems require individuals to manually log instrument usage. Automated tracking systems typically require augmentation of the medical device to allow tracking. For example, certain medical devices may include embedded or attached radio frequency identifier (RFID) tags, retro-reflective infrared (IR) tracking tags, or other tracking tags. However, some tracking tags are not compatible with autoclave sterilization.

SUMMARY

According to one aspect of the disclosure, a system for medical device usage monitoring includes a capture device, a base station device, and an analytics server. The capture device includes a camera device and a capture engine to capture image capture data. The image capture data is indicative of a time series of images representing a monitored location of an operating room. The capture engine is further to transmit the image capture data to the base station device. The base station device includes a capture interface to receive the image capture data from the image capture device, a recognition engine to recognize a medical device in the image capture data with a machine learning model to generate recognition data, and an analytics interface to transmit the recognition data to the analytics server. The recognition data is indicative of whether the medical device is represented at the monitored location at a corresponding time in the image capture data. The analytics server includes a recognition interface to receive the recognition data from the base station device and an inference engine to generate medical device usage data based on the recognition data. The medical device usage data is indicative of a usage label associated with the medical device for each corresponding time of the recognition data.

In an embodiment, to recognize the medical device comprises to input the image capture data to a single-pass convolutional neural network. In an embodiment, to recognize the medical device comprises to determine whether any of a predetermined library of medical devices is represented in the image capture data. In an embodiment, the recognition data comprises a binary vector, and wherein each bit of the binary vector corresponds to a medical device of the predetermined library of medical devices.

In an embodiment, to recognize the medical device comprises to identify a type of the medical device and a size of the medical device. In an embodiment, the type comprises a surgical reamer, a shell inserter, a shell trial, or a trial liner. In an embodiment, the size comprises a dimension in millimeters. In an embodiment, to recognize the medical device comprises to determine a state of a medical device represented in the image capture data.

In an embodiment, to transmit the image capture data comprises to wirelessly transmit the image capture data. In an embodiment, the capture interface is further to receive second image capture data from a second image capture device, wherein the second image capture data is indicative of a time series of images representing a second monitored location of the operating room, and the recognition engine is further to recognize the medical device in the second image capture data with the machine learning model to generate the recognition data, wherein the recognition data is further indicative of whether the medical device is represented at the corresponding time in the second image capture data.

In an embodiment, the usage label is indicative of the monitored location or an in-use status. In an embodiment, to generate the medical device usage data comprises, for each corresponding time of the recognition data, to determine whether the recognition data indicates that the medical device is represented at the monitored location; generate the usage label indicative of the monitored location in response to a determination that the recognition data indicates that the medical device is represented at the monitored location; and generate the usage label indicative of the in-use status in response to a determination that the recognition data indicates that the medical device is not represented at the monitored location.

In an embodiment, the recognition data is further indicative of whether the medical device is represented at a second monitored location at the corresponding time. To generate the medical device usage data comprises, for each corresponding time of the recognition data, to determine whether the recognition data indicates that the medical device is represented at any corresponding monitored location of the monitored location and the second monitored location; generate the usage label indicative of the corresponding monitored location in response to a determination that the recognition data indicates that the medical device is represented at any corresponding monitored location; and generate the usage label indicative of the in-use status in response to a determination that the recognition data indicates that the medical device is not represented at any corresponding monitored location.

In an embodiment, the analytics server further comprises an analytics engine to analyze the medical device usage data to generate analytical usage data. In an embodiment, the recognition interface is further to receive recognition data from a second computing device; and to generate the medical device usage data comprises to generate the medical device usage data based on the recognition data received from the computing device and the recognition data received from the second computing device.

In an embodiment, to analyze the medical device usage data comprises to determine a medical device sequence and a frequency based on the medical device usage data. In an embodiment, to analyze the medical device usage data comprises to perform pattern recognition with the medical device usage data. In an embodiment, to analyze the medical device usage data comprises to perform anomaly detection with the medical device usage data. In an embodiment, the analytics server further comprises an analytics portal interface to expose the analytical usage data to a client device.

According to another aspect, a method for medical device usage monitoring includes receiving, by a computing device, image capture data from an image capture device, wherein the image capture data is indicative of a time series of images representing a monitored location of an operating room; recognizing, by the computing device, a medical device in the image capture data with a machine learning model to generate recognition data, wherein the recognition data is indicative of whether the medical device is represented at the monitored location at a corresponding time in the image capture data; and transmitting, by the computing device, the recognition data to a remote analytics server.

In an embodiment, recognizing the medical device comprises inputting the image capture data to a single-pass convolutional neural network. In an embodiment, recognizing the medical device comprises determining whether any of a predetermined library of medical devices is represented in the image capture data. In an embodiment, the recognition data comprises a binary vector, and wherein each bit of the binary vector corresponds to a medical device of the predetermined library of medical devices.

In an embodiment, recognizing the medical device comprises identifying a type of the medical device and a size of the medical device. In an embodiment, the type comprises a surgical reamer, a shell inserter, a shell trial, or a trial liner. In an embodiment, the size comprises a dimension in millimeters. In an embodiment, recognizing the medical device comprises determining a state of a medical device represented in the image capture data.

In an embodiment, the method further includes capturing, by the image capture device, the image capture data; and transmitting, by the image capture device, the image capture data to the computing device. In an embodiment, transmitting the image capture data comprises wirelessly transmitting the image capture data.

In an embodiment, the method further includes receiving, by the computing device, second image capture data from a second image capture device, wherein the second image capture data is indicative of a time series of images representing a second monitored location of the operating room; and recognizing, by the computing device, the medical device in the second image capture data with the machine learning model to generate the recognition data, wherein the recognition data is further indicative of whether the medical device is represented at the corresponding time in the second image capture data.

In an embodiment, the method further includes receiving, by the analytics server, the recognition data from the computing device; and generating, by the analytics server, medical device usage data based on the recognition data, wherein the medical device usage data is indicative of a usage label associated with the medical device for each corresponding time of the recognition data. In an embodiment, the usage label is indicative of the monitored location or an in-use status. In an embodiment, generating the medical device usage data comprises, for each corresponding time of the recognition data determining whether the recognition data indicates that the medical device is represented at the monitored location; generating the usage label indicative of the monitored location in response to determining that the recognition data indicates that the medical device is represented at the monitored location; and generating the usage label indicative of the in-use status in response to determining that the recognition data indicates that the medical device is not represented at the monitored location.

In an embodiment, the recognition data is further indicative of whether the medical device is represented at a second monitored location at the corresponding time. Generating the medical device usage data comprises, for each corresponding time of the recognition data, determining whether the recognition data indicates that the medical device is represented at any corresponding monitored location of the monitored location and the second monitored location; generating the usage label indicative of the corresponding monitored location in response to determining that the recognition data indicates that the medical device is represented at any corresponding monitored location; and generating the usage label indicative of the in-use status in response to determining that the recognition data indicates that the medical device is not represented at any corresponding monitored location.

In an embodiment, the method further includes analyzing, by the analytics server, the medical device usage data to generate analytical usage data. In an embodiment, the method further includes receiving, by the analytics server, recognition data from a second computing device; wherein generating the medical device usage data comprises generating the medical device usage data based on the recognition data received from the computing device and the recognition data received from the second computing device.

In an embodiment, analyzing the medical device usage data comprises determining a medical device sequence and a frequency based on the medical device usage data. In an embodiment, analyzing the medical device usage data comprises performing pattern recognition with the medical device usage data. In an embodiment, analyzing the medical device usage data comprises performing anomaly detection with the medical device usage data. In an embodiment, the method further includes exposing, by the analytics server, the analytical usage data to a client device via an analytics interface.

BRIEF DESCRIPTION OF THE DRAWINGS

The detailed description particularly refers to the following figures, in which:

FIG. 6 is a simplified flow diagram of at least one embodiment of a method for recognizing medical devices in the image capture data that may be executed by a base station device of FIGS. 1-3;

FIG. 7 is a simplified flow diagram of at least one embodiment of a method for analyzing recognition data that may be executed by an analytics server of FIGS. 1-3;

FIG. 8 is a simplified flow diagram of at least one embodiment of a method for inferring medical device usage data that may be executed by the analytics server of FIGS. 1-3;

FIG. 11 is a schematic diagram illustrating exemplary usage data that may be generated by the analytics server of FIGS. 1-3;

DETAILED DESCRIPTION OF THE DRAWINGS

Figure 1:
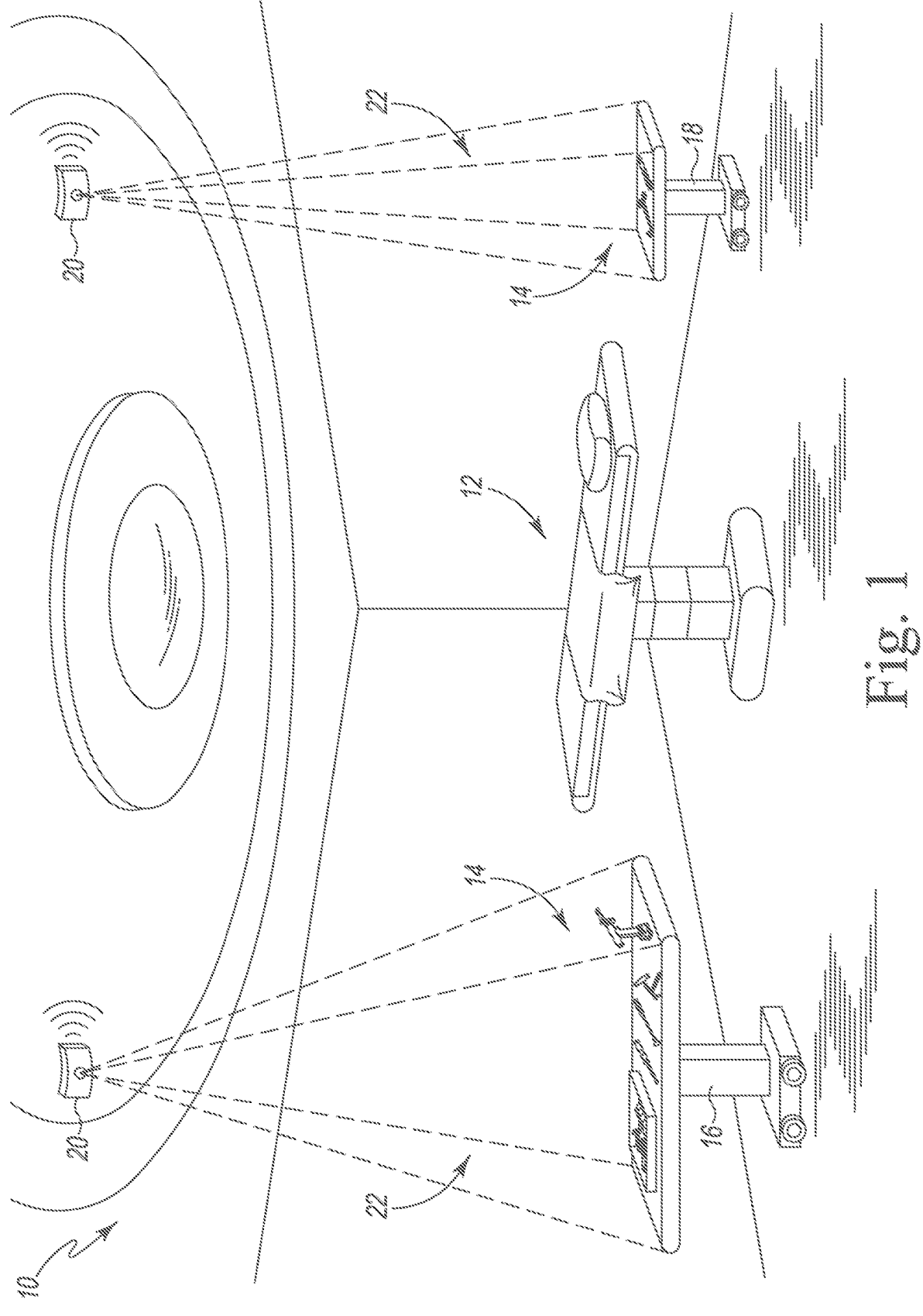
FIG. 1 is a schematic diagram of at least one embodiment of a system for medical device usage tracking installed in an operating room.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the medical devices described herein as well as in reference to the patient's natural anatomy. Such terms have well-understood meanings in both the study of anatomy and the field of medicine, including orthopaedics. Use of such anatomical reference terms in the written description and claims is intended to be consistent with their well-understood meanings unless noted otherwise.

Referring now to FIG. 1, an illustrative operating room 10 includes an operating table 12. During a surgical procedure, a surgeon uses multiple medical devices 14, including surgical instruments, surgical implants or prosthetics, or other medical devices, which are represented schematically in FIG. 1. The medical devices 14 may include, for example, surgical reamers, broaches, impactors and impaction handles, prosthetic trials, trial liners, drill guides, cutting blocks, surgical saws, ligament balancers, or other medical devices used in the performance of an orthopaedic surgical procedure.

The operating room 10 also includes one or more tables or other locations upon which the medical devices 14 may be stored, staged, or otherwise arranged. For example, in the illustrative example shown in FIG. 1, the operating room 10 includes an entry or "clean" table 16 and a used or "dirty" table 18. During a procedure, a nurse or other assistant may move medical devices 14 from the entry table 16 to the operating table 12, and then from the operating table 12 to the used table 18. Of course, the operating room 10 may include any other number and/or arrangement of tables, trays, or other locations, and in one or more different surgical flows may be used.

The operating room 10 also includes one or more capture devices 20 that are fixed to a structure of the operating room 10. In the illustrative embodiment shown in FIG. 1, there are two capture devices 20 fixed to the ceiling of the operating room 10. In other embodiments, the capture devices 20 may be removably or non-removably fixed to any stand, table, wall, or other structure positioned in the operating room 10. Additionally, although illustrated as including two capture devices 20, it should be understood that in some embodiments the system may include a different number of capture devices 20, such as a single capture device 20 or more than two capture devices 20. As described further below, each capture device 20 includes a camera capable of capturing images in a field of view 22. Each field of view 22 defines a monitored location within the operating room 10. Illustratively, each of the tables 16, 18 is positioned in a monitored location. Note, however, that the surgical table 12 is not positioned in a monitored location.

In use, and as described further below, the capture devices 20 capture images of the monitored locations and transmit those images wirelessly to a base station device, which may be located at the same facility as the operating room 10 (e.g., within the same hospital). Using a trained machine learning model, the base station device recognizes any medical devices imaged within the monitored location. The base station device transmits recognition data (e.g., binary recognition date) to a remote analytics server, which infers medical device usage based on the recognition data and may perform additional analysis of the usage data, including pattern detection and anomaly detection. Thus, the system shown in FIG. 1 is capable of tracking medical device usage without requiring that the medical devices be augmented with RFID tags or other tracking devices. Accordingly, the system of FIG. 1 is capable of tracking usage patterns for medical devices that have already been distributed in the field, without requiring modification of existing medical devices or manufacture of new medical devices. Additionally, the system of FIG. 1 is capable of inferring medical device use without storing captured images and without capturing images of the surgical table itself. Further, the system of FIG. 1 may have a modular architecture and thus may be capable of integrating other tracking technologies (e.g., RFID tracking, IR tracking, or other tracking systems).

Figure 2:
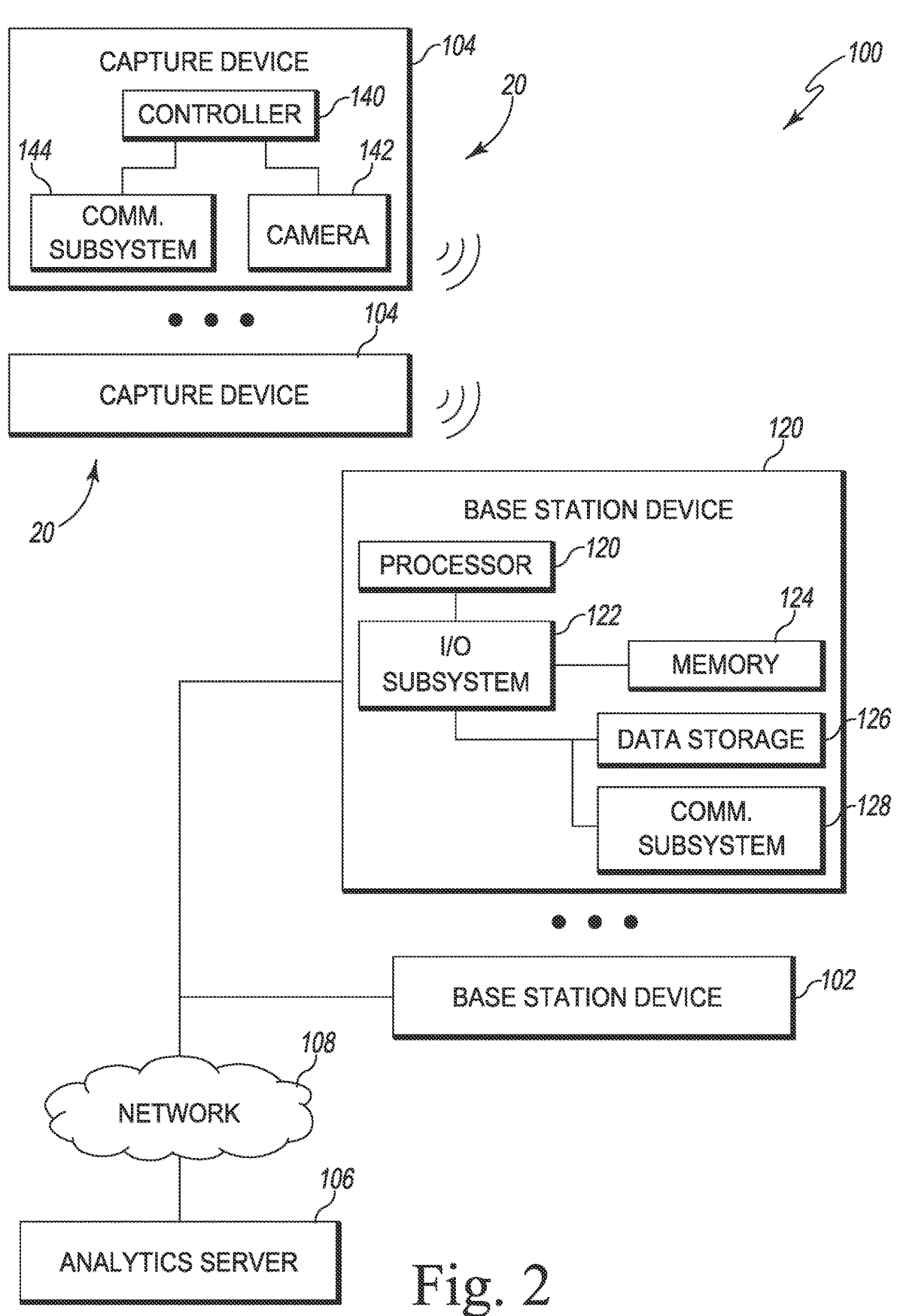
FIG. 2 is a simplified block diagram of at least one embodiment of the system of FIG. 1.

Referring now to FIG. 2, an illustrative system 100 includes one or more base station devices 102 that are in wireless communication with one or more capture devices 104 and are in communication with an analytics server 106 over a network 108. In use, the system 100 may be installed in or otherwise used with an operating room 10 as shown in FIG. 1. In particular, the capture devices 20 shown in FIG. 1 may be embodied as the capture devices 104.

Each base station device 102 may be embodied as any type of device capable of performing the functions described herein. For example, a base station device 102 may be embodied as, without limitation, a desktop computer, a workstation, a network appliance, a web appliance, a server, a rack-mounted server, a blade server, a laptop computer, a tablet computer, a smartphone, a consumer electronic device, a distributed computing system, a multiprocessor system, and/or any other computing device capable of performing the functions described herein. As shown in FIG. 1, the illustrative base station device 102 includes a processor 120, an I/O subsystem 122, memory 124, a data storage device 126, and a communication subsystem 128. Of course, the base station device 102 may include other or additional components, such as those commonly found in a server computer (e.g., various input/output devices), in other embodiments. Additionally, in some embodiments, one or more of the illustrative components may be incorporated in, or otherwise form a portion of, another component. For example, the memory 124, or portions thereof, may be incorporated in the processor 120 in some embodiments.

The processor 120 may be embodied as any type of processor or compute engine capable of performing the functions described herein. For example, the processor may be embodied as a single or multi-core processor(s), digital signal processor, microcontroller, or other processor or processing/controlling circuit. Similarly, the memory 124 may be embodied as any type of volatile or non-volatile memory or data storage capable of performing the functions described herein. In operation, the memory 124 may store various data and software used during operation of the base station device 102 such as operating systems, applications, programs, libraries, and drivers. The memory 124 is communicatively coupled to the processor 120 via the I/O subsystem 122, which may be embodied as circuitry and/or components to facilitate input/output operations with the processor 120, the memory 124, and other components of the base station device 102. For example, the I/O subsystem 122 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 122 may form a portion of a system-on-a-chip (SoC) and be incorporated, along with the processor 120, the memory 124, and other components of the base station device 102, on a single integrated circuit chip.

The data storage device 126 may be embodied as any type of device or devices configured for short-term or long-term storage of data such as, for example, memory devices and circuits, memory cards, hard disk drives, solid-state drives, or other data storage devices. The communication subsystem 128 of the base station device 102 may be embodied as any communication circuit, device, or collection thereof, capable of enabling communications between the base station device 102, the capture devices 104, the analytics server 106, and other remote devices. The communication subsystem 128 may be configured to use any one or more communication technology (e.g., wireless or wired communications) and associated protocols (e.g., Ethernet, Bluetooth®, Wi-Fi®, WiMAX, 3G LTE, 5G, etc.) to effect such communication.

Each of the capture devices 104 may be embodied as any type of device capable of performing the functions described herein. For example, a capture device 104 may be embodied as an inexpensive device that may be powered by one or more rechargeable or non-rechargeable batteries. As the capture device 104 is capable of wireless communication, the capture device 104 may be installed or otherwise used in an operating room 10 without requiring a power connection, a network connection, or other additional infrastructure. In some embodiments, each capture device 104 may be disposable (e.g., upon depletion of the battery), which may further reduce required maintenance and/or operating costs.

As shown in FIG. 2, the capture device 104 may include a controller 140, a camera 142, and a communication subsystem 144. The controller 140 may be embodied as any type of controller or compute engine capable of performing the functions described herein. For example, the controller may be embodied as a microcontroller, a digital signal processor, a single or multi-core processor(s), a system on a chip (SoC), or other processor or processing/controlling circuit.

The camera 142 may be embodied as a digital camera or other digital imaging device integrated with the capture device 104 or otherwise communicatively coupled thereto. The camera 142 includes an electronic image sensor, such as an active-pixel sensor (APS), e.g., a complementary metal-oxide-semiconductor (CMOS) sensor, or a charge-coupled device (CCD). The camera 142 may be used to capture image data including, in some embodiments, capturing still images or video images.

The communication subsystem 144 of the capture device 104 may be embodied as any communication circuit, device, or collection thereof, capable of enabling communications between the capture device 104 and the base station device 102, and other remote devices. The communication subsystem 144 is illustratively configured to use any one or more wireless communication technology and associated protocols (e.g., Bluetooth®, Wi-Fi®, WiMAX, 3G LTE, 5G, etc.) to effect such communication. Additionally or alternatively, in some embodiments the communication subsystem 144 may be capable of wired communications (e.g. Ethernet).

The analytics server 106 be embodied as any type of computation or computer device capable of performing the functions described herein, including, without limitation, a server, a rack-mounted server, a blade server, a computer, a workstation, a laptop computer, a notebook computer, a tablet computer, a mobile computing device, a wearable computing device, a multiprocessor system, a network appliance, a web appliance, a distributed computing system, a processor-based system, and/or a consumer electronic device. Thus, the analytics server 106 includes components and devices commonly found in a computer or similar computing device, such as a processor, an I/O subsystem, a memory, a data storage device, and/or communication circuitry. Those individual components of the analytics server 106 may be similar to the corresponding components of the base station device 102, the description of which is applicable to the corresponding components of the analytics server 106 and is not repeated herein so as not to obscure the present disclosure. Additionally, in some embodiments, the analytics server 106 may be embodied as a "virtual server" formed from multiple computing devices distributed across the network 108 and operating in a public or private cloud. Accordingly, although the analytics server 106 is illustrated in FIG. 2 as embodied as a single computing device, it should be appreciated that the analytics server 106 may be embodied as multiple devices cooperating together to facilitate the functionality described below.

As discussed further below, the base station devices 102, the capture devices 104, and/or the analytics server 106 may be configured to transmit and receive data with each other and/or other devices of the system 100 over the network 108. The network 108 may be embodied as any number of various wired and/or wireless networks. For example, the network 108 may be embodied as, or otherwise include, a wired or wireless local area network (LAN), a wired or wireless wide area network (WAN), a cellular network, and/or a publicly-accessible, global network such as the Internet. As such, the network 108 may include any number of additional devices, such as additional computers, routers, stations, and switches, to facilitate communications among the devices of the system 100.

Figure 3:
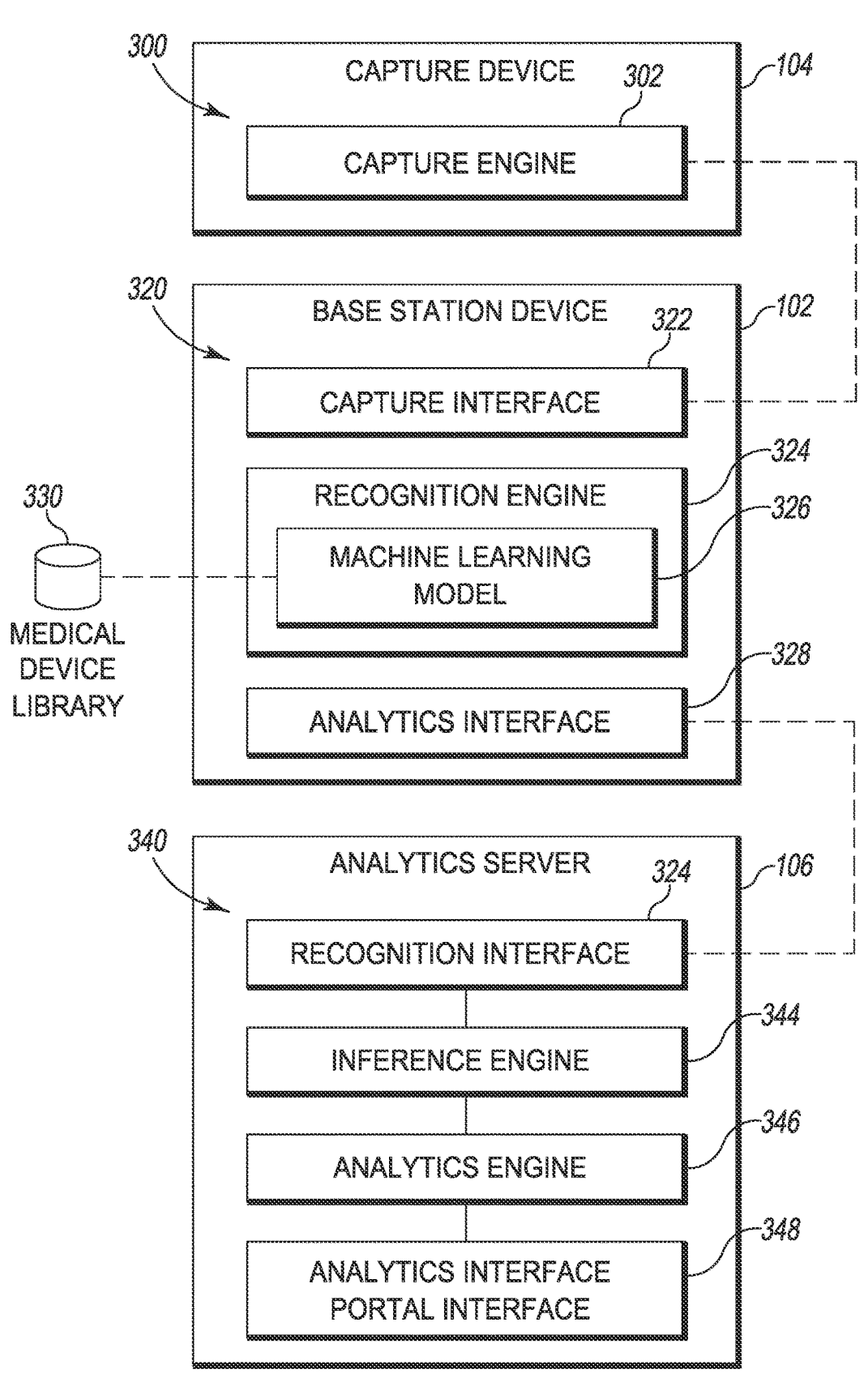
FIG. 3 is a simplified block diagram of various environments that may be established by the system of FIGS. 1-2.

Referring now to FIG. 3, in the illustrative embodiment, the capture device 104 establishes an environment 300 during operation. The illustrative environment 300 includes a capture engine 302, which may be embodied as hardware, firmware, software, or a combination thereof. As such, in some embodiments, one or more of the components of the environment 300 may be embodied as circuitry or a collection of electrical devices (e.g., capture engine circuitry 302). It should be appreciated that, in such embodiments, one or more of those components may form a portion of the controller 140, the camera 142, the communication subsystem 144, and/or other components of the capture device 104.

The capture engine 302 is configured to capture image capture data using the camera 142. The image capture data is indicative of a time series of images representing a monitored location of an operating room (e.g., the operating room 10). The capture engine 302 is further configured to transmit the image capture data to the base station device 102. The image capture data may be transmitted wirelessly.

Still referring to FIG. 3, in the illustrative embodiment, the base station device 102 establishes an environment 320 during operation. The illustrative environment 320 includes a capture interface 322, a recognition engine 324, and an analytics interface 328. The various components of the environment 320 may be embodied as hardware, firmware, software, or a combination thereof. As such, in some embodiments, one or more of the components of the environment 320 may be embodied as circuitry or a collection of electrical devices (e.g., capture interface circuitry 322, recognition engine circuitry 324, and/or analytics interface circuitry 328). It should be appreciated that, in such embodiments, one or more of those components may form a portion of the processor 120, the I/O subsystem 122, and/or other components of the base station device 102.

The capture interface 322 is configured to receive image capture data from one or more image capture devices 104. As described above, the image capture data is indicative of a time series of images representing a monitored location of the operating room associated with the respective image capture device 104.

The recognition engine 324 is configured to recognize one or more medical devices in the image capture data using a machine learning model 326 to generate recognition data. The machine learning model 326 may be embodied as, for example, a single-pass convolutional neural network. The recognition data is indicative of whether the medical device is represented at the monitored location at a corresponding time in the image capture data. Recognizing the medical device may include determining whether any medical device of a predetermined library 330 of medical devices is represented in the image capture data. The machine learning model 326 may be trained using the medical device library 330 as described further below. In some embodiments, the recognition data includes a binary vector. Each bit of the binary vector corresponds to a medical device of the predetermined library 330 of medical devices.

In some embodiments, recognizing the medical device may include identifying a type of the medical device and a size of the medical device. The type may be, for example, a surgical reamer, a shell inserter, a shell trial, or a trial liner. The size may be a dimension in millimeters. In some embodiments, recognizing the medical device may include determining a state of a medical device represented in the image capture data.

The analytics interface 328 is configured to transmit the recognition data to the analytics server 106. The recognition data may also be transmitted wirelessly.

Still referring to FIG. 3, in the illustrative embodiment, the analytics server 106 establishes an environment 340 during operation. The illustrative environment 340 includes a recognition interface 342, an inference engine 344, an analytics engine 346, and an analytics portal interface 348. The various components of the environment 340 may be embodied as hardware, firmware, software, or a combination thereof. As such, in some embodiments, one or more of the components of the environment 340 may be embodied as circuitry or a collection of electrical devices (e.g., recognition interface circuitry 342, inference engine circuitry 344, analytics engine circuitry 346, and/or analytics portal interface circuitry 348). It should be appreciated that, in such embodiments, one or more of those components may form a portion of the processor, the I/O subsystem, and/or other components of the analytics server 106.

The recognition interface 342 is configured to receive the recognition data from one or more base station devices 102. As described above, the recognition data may be a binary vector indicating which medical devices were recognized.

The inference engine 344 is configured to generate medical device usage data based on the recognition data. The medical device usage data is indicative of a usage label associated with the medical device for each corresponding time of the recognition data. In some embodiments, the usage label may be indicative of the monitored location, an in-use status, or a device state. Generating the medical device usage data may include, for each corresponding time of the recognition data, determining whether the recognition data indicates that the medical device is represented at a monitored location, generating the usage label indicative of the monitored location if the recognition data indicates that the medical device is represented at the monitored location, and generating the usage label indicative of the in-use status if the recognition data indicates that the medical device is not represented at the monitored location. Generating the medical device usage data may include determining whether the medical device is represented at any monitored location at the corresponding time and generating the usage label indicative of the in-use status if the recognition data indicates that the medical device is not represented at any corresponding monitored location.

The analytics engine 346 is configured to analyze the medical device usage data to generate analytical usage data. Analyzing the medical device usage data may include determining a medical device sequence and a frequency based on the medical device usage data, performing pattern recognition with the medical device usage data, or performing anomaly detection with the medical device usage data.

The analytics portal interface 348 is configured to expose the analytical usage data to a client device. For example, the analytical usage data may be exposed via a web site, a web portal, a mobile application, or other application interface.

Figure 4:
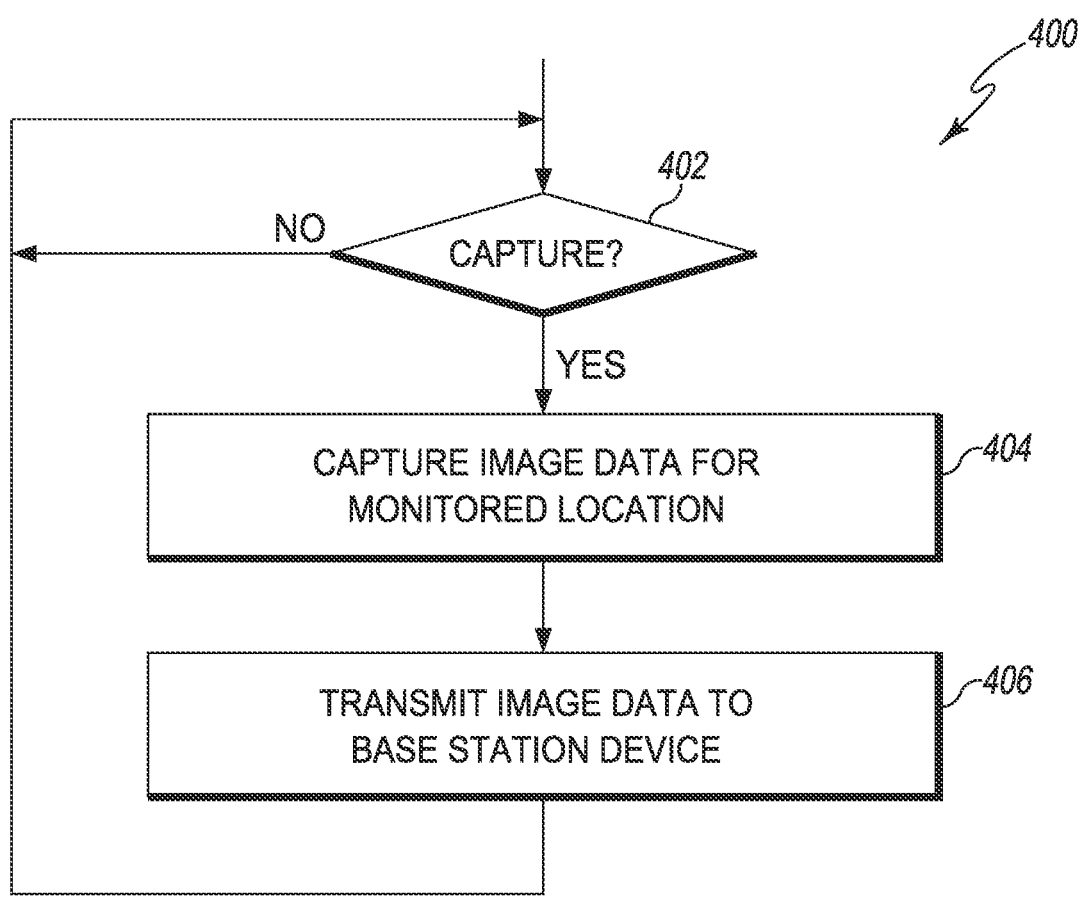
FIG. 4 is a simplified flow diagram of at least one embodiment of a method for capturing image data that may be executed by a capture device of FIGS. 1-3.

Referring now to FIG. 4, in use, a capture device 104 may execute a method 400 for capturing image data. It should be appreciated that, in some embodiments, the operations of the method 400 may be performed by one or more components of the environment 300 of the capture device 104 as shown in FIG. 3. The method 400 begins with block 402, in which the capture device 104 determines whether to begin capturing images. The capture device 104 may capture images, for example, in response to a user activation command such as a button press. As another example, the capture device 104 may capture images in response to detecting motion, for example using the camera 142 or another motion sensing component. In some embodiments, the capture device 104 may capture images in response to a remote command received via wireless network communications. If the capture device 104 determines not to capture images, the method 400 loops back to block 402 to continue waiting to capture images. If the capture device 104 determines to capture images, the method 400 advances to block 404.

In block 404, the capture device 104 captures image data for a monitored location. As described above, the monitored location may correspond to an entry table 16, a used table 18, or any other sterile or non-sterile location within an operation room, other than the surgical table. The capture device 104 uses the camera 142 to capture the image data. The image data may be embodied as a time series of still images, which may be captured as still images, extracted from video data, or otherwise captured by the capture device 104. Each captured image is associated with a timestamp, and each image may be captured at roughly regular intervals (e.g., every minute, every 30 seconds, or other interval). In some embodiments, the capture device 104 may intelligently determine dynamic intervals for capturing images, which may reduce power consumption.

In block 406, the capture device 104 transmits the image data to the base station device 104. The capture device 104 may transmit the image data wirelessly, for example via Wi-Fi, Bluetooth, Bluetooth Low Energy (BLE) or other wireless communications technology. After transmitting the image data, the base station device 102 may perform object recognition and other image processing tasks. Accordingly, the capture device 104 is not required to retain the image data, and thus each capture device 104 may have relatively low data storage requirements. After transmitting the captured image data, the method 400 loops back to block 402 to continue capturing image data.

Figure 5:
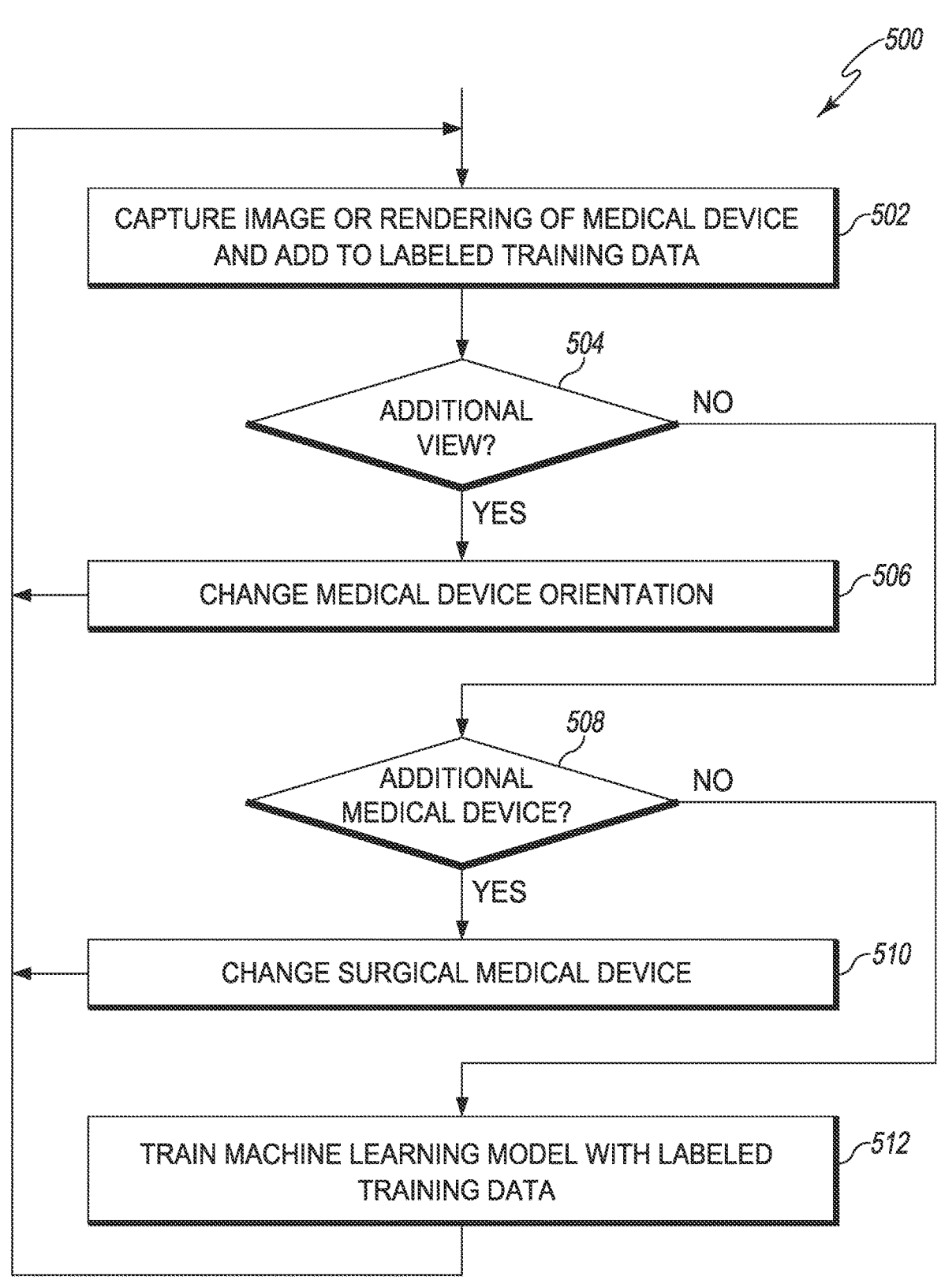
FIG. 5 is a simplified flow diagram of at least one embodiment of a method for training a machine learning model that may be used by a base station device of FIGS. 1-3.

Referring now to FIG. 5, a method 500 for training the machine learning model 326 of the base station device 102 is shown. It should be appreciated that, in some embodiments, the operations of the method 500 may be performed by the base station device 102, for example to refine the machine learning model 326 as it is in use. Additionally or alternatively, in some embodiments, the operations of the method 500 may be performed prior to deploying the trained machine learning model 326 to the base station device 102, for example by a development workstation or by a cloud system. The method 500 begins in block 502, in which an image or a high fidelity rendering of a medical device is captured and added to a labeled training data set such as the medical device library 330. The image may be captured, for example, by a capture device 104, by a camera device similar to the capture device 104, or by another image capture device. In some embodiments, the image may be captured or otherwise selected from image data captured during performance of a surgical procedure. For example, the image may correspond to an unidentified medical device captured during a surgical procedure. In some embodiments, the image may be captured manually ahead of time, for example while preparing the medical device library 330. As described above, in some embodiments the image may be captured or otherwise generated as a high fidelity rendering of the medical device rather than as a photograph or other sensed image data. For example, the image may be rendered based on a three-dimensional model, a CAD drawing, or other representation of the medical device. As described above, the captured image is included in a set of labeled training data. The captured image may be labeled with, for example, a particular medical device identifier (e.g., a product code or other identifier), a medical device type, a medical device size, or other identifier.

In block 504, it is determined whether an additional view of the medical device should be captured. If not, the method 500 branches ahead to block 508, described below. If additional views should be captured, the method 500 advances to block 506, in which the orientation, configuration, or environmental complexity of the medical device is changed. For example, a technician may flip, rotate, or otherwise change the orientation of the medical device. In some embodiments, the medical device may be held in position using one or more armatures, tables, stages, or other holding devices. Those holding devices may allow a technician to quickly arrange the medical device in a desired orientation for image capture. As another example, to change the configuration of the medical device, a technician may change the state of the medical device, for example by moving a pair of scissors from an open state to a closed state. Environmental complexity may refer to other known medical devices partially occluding the subject medical device (e.g., a pair of scissors laying on top of an impactor handle). Environmental complexity may also mean unknown objects partially occluding the subject medical device (e.g., a hand, an unregister medical device, or other object obscuring the impactor handle). After changing the orientation, configuration, or environmental complexity, the method 500 loops back to block 502, in which additional images of the medical device are captured.

Referring back to block 504, if no additional views should be captured, the method 500 branches to block 508, in which it is determined whether additional medical devices should be captured. If not, the method 500 branches ahead to block 512, described below. If additional medical devices should be captured, the method 500 advances to block 510, in which the medical device being captured is changed. For example, a technician may select a new medical device and place that medical device within the field of view of a capture device 104 or other camera device. After changing the medical device, the method 500 loops back to block 502 to continue capturing images of the new medical device. The method 500 may continue capturing images for the labeled training set until sufficient images are captured for all of the medical devices in the medical device library 330. The medical device library 330 may include data for all medical devices currently in a manufacturer's catalog, for all medical devices expected to be used in a particular surgical procedure, for medical devices that are no longer manufactured but may still be in use, or for any other predetermined set of medical devices.

Referring back to block 508, if no additional medical devices remain for capture, the method 500 branches to block 512, in which a machine learning model is trained with the labeled training data. For example, the machine learning model 326 may be trained using the medical device library 330. Training the machine learning model 326 allows the model 326 to be used to recognize medical devices that are included in the medical device library 330. The machine learning model 326 may be embodied as a single-pass convolutional neural network (CNN) such as a YOLO v5 model or another object recognition model. The machine learning model 326 may be trained using an appropriate training algorithm such as backpropagation with gradient descent. After training, the trained machine learning model 326 may be deployed to one or more base station devices 102 for production use. After training is completed, the method 500 loops back to block 502, in which additional training data may be captured and the machine learning model 326 may continue to be trained.

Referring now to FIG. 6, in use, a base station device 102 may execute a method 600 for recognizing medical devices in the image capture data. It should be appreciated that, in some embodiments, the operations of the method 600 may be performed by one or more components of the environment 320 of the base station device 102 as shown in FIG. 3. The method 600 begins with block 602, in which the base station device 102 receives image capture data from a capture device 104. As described above, the image capture data may be embodied as a time series of still images of a monitored location in an operating room, such as one of the tables 16, 18 shown in FIG. 1. Each image in the image capture data is associated with a corresponding timestamp. As described above, the capture device 104 may be located in the same facility (e.g., the same hospital) as the base station device 102. Accordingly, the image capture data may be received wirelessly.

In block 604, the base station device 102 recognizes medical devices in the image data using the trained machine learning model 326. In particular, the base station device 102 may input each frame of the image capture data to the machine learning model 326, which outputs an indication of whether one or more medical devices were recognized in the image frame. For example, the machine learning model 326 may output a binary vector with each index of the binary vector corresponding to a particular medical device, type of medical device, or other recognition result. Set bits in the binary vector indicate the presence of the corresponding medical device.

Figure 9:
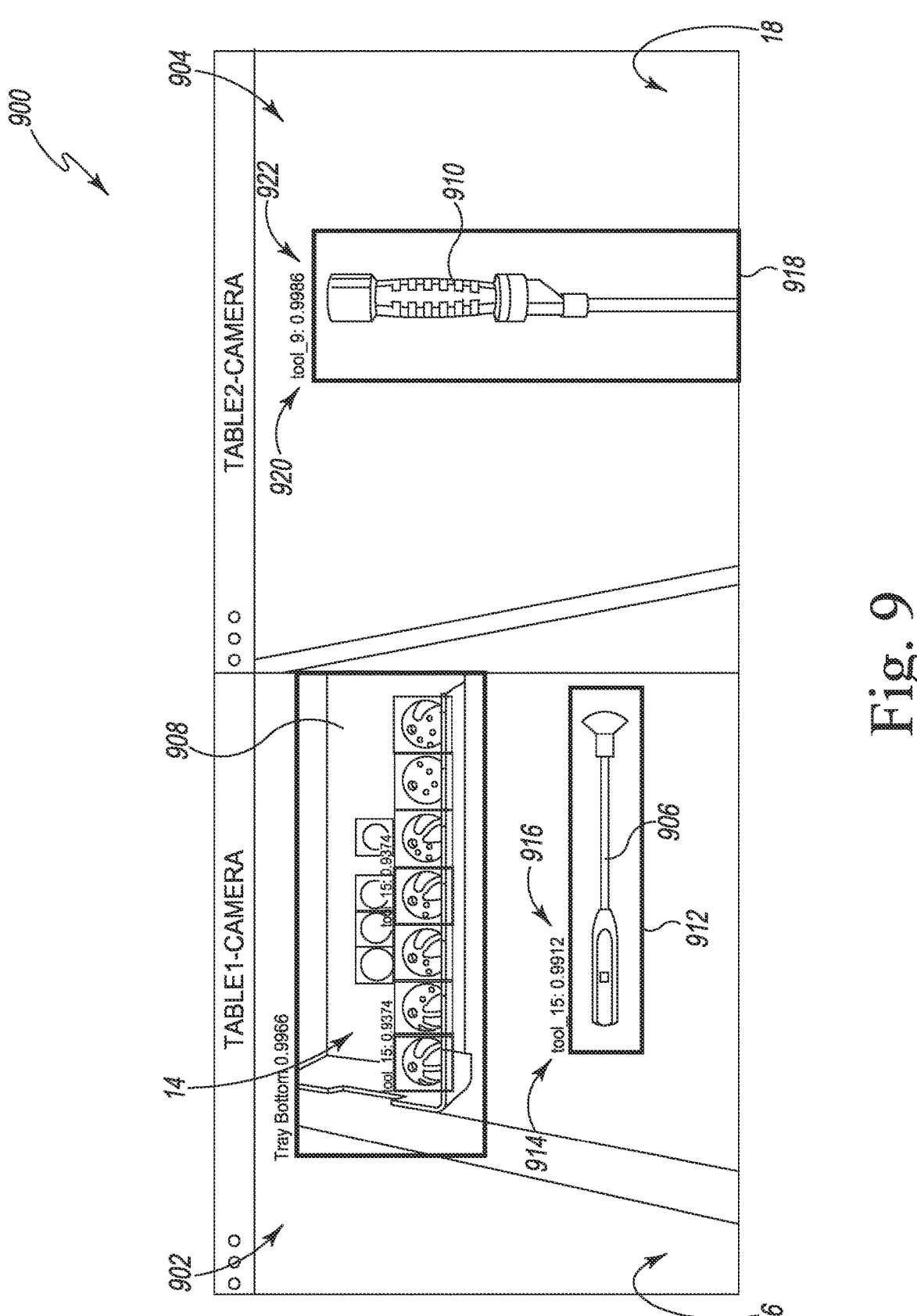
FIG. 9 is a schematic diagram illustrating exemplary image recognition that may be performed by the base station device of FIGS. 1-3.

In some embodiments, in block 606, the base station device 102 may recognize the medical devices using a single-pass convolutional neural network (CNN) such as a YOLO v5 model, or another object recognition model. In some embodiments, in block 608 the base station device 102 may determine a medical device type or identity and a corresponding bounding box for each medical device recognized in the frame. The medical device type may be a category of related medical devices for which there are multiple sizes, styles, or other variations (e.g., a surgical reamer, a trial shell, a trial insert, or other medical device type). The medical device identity may be, for example, a particular product code or other catalog entry (e.g., an identifier for a 42 mm surgical reamer, a 42 mm trial shell, or other specific medical device). In some embodiments, the base station device 102 may determine a medical device type and a corresponding size, which may be used as an ordered pair to identify a particular medical device. The bounding box may identify the particular location within the captured image in which the recognized medical device appears. In the illustrative embodiment, the base station device 102 may disregard the bounding box. One potential embodiment of medical device recognition that may be performed by the base station device 102 is illustrated in FIG. 9 and described further below.

In some embodiments, in block 610 the base station device 102 may determine a medical device state. For example, a medical device such as a surgical tray or a case may be identified as being opened or closed. In some embodiments, the medical device state may be implemented as multiple different medical device categories. For example, in an illustrative embodiment, the machine learning model 326 may be trained with the medical device tray opened and closed as two different medical device types (e.g., as TrayClosed or TrayOpened).

In block 612, the base station device 102 stores the recognition data with timestamp information associated with the image capture device. For example, for each timestamp represented in the image capture data, the base station device 102 may store a corresponding binary vector indicating the medical devices that were recognized in the image capture data at that timestamp.

After storing the binary vector, the base station device 102 may not continue to store the captured image data. However, in some embodiments, the base station device 102 may store some or all of the captured image data, for example to perform retraining or manual labeling. Continuing that example, in some embodiments the base station device 102 may store captured image data that includes an unrecognized medical device or a medical device with a low confidence rating. This stored image data may be used for relearning or otherwise refining the machine learning model 326 as described above in connection with FIG. 5.

In block 614, the base station device 102 determines whether to perform medical device recognition for additional capture devices 104. As described above, each operating room 10 may include multiple capture devices 104 that each capture image data indicative of a particular monitored location within the operating room 10. Additionally or alternatively, in some embodiments the base station device 102 may receive image data from capture devices 104 positioned in multiple operating rooms 10 within a facility. For example, a hospital may include multiple operating rooms 10 that each respectively include multiple capture devices 104, and the base station device 102 may receive and process image capture data from each of those capture devices 104. If the base station device 102 determines to perform recognition for additional capture devices 104, the method 600 loops back to block 602. If the base station device 102 determines not to perform additional recognition, the method 600 advances to block 616.

Figure 10:
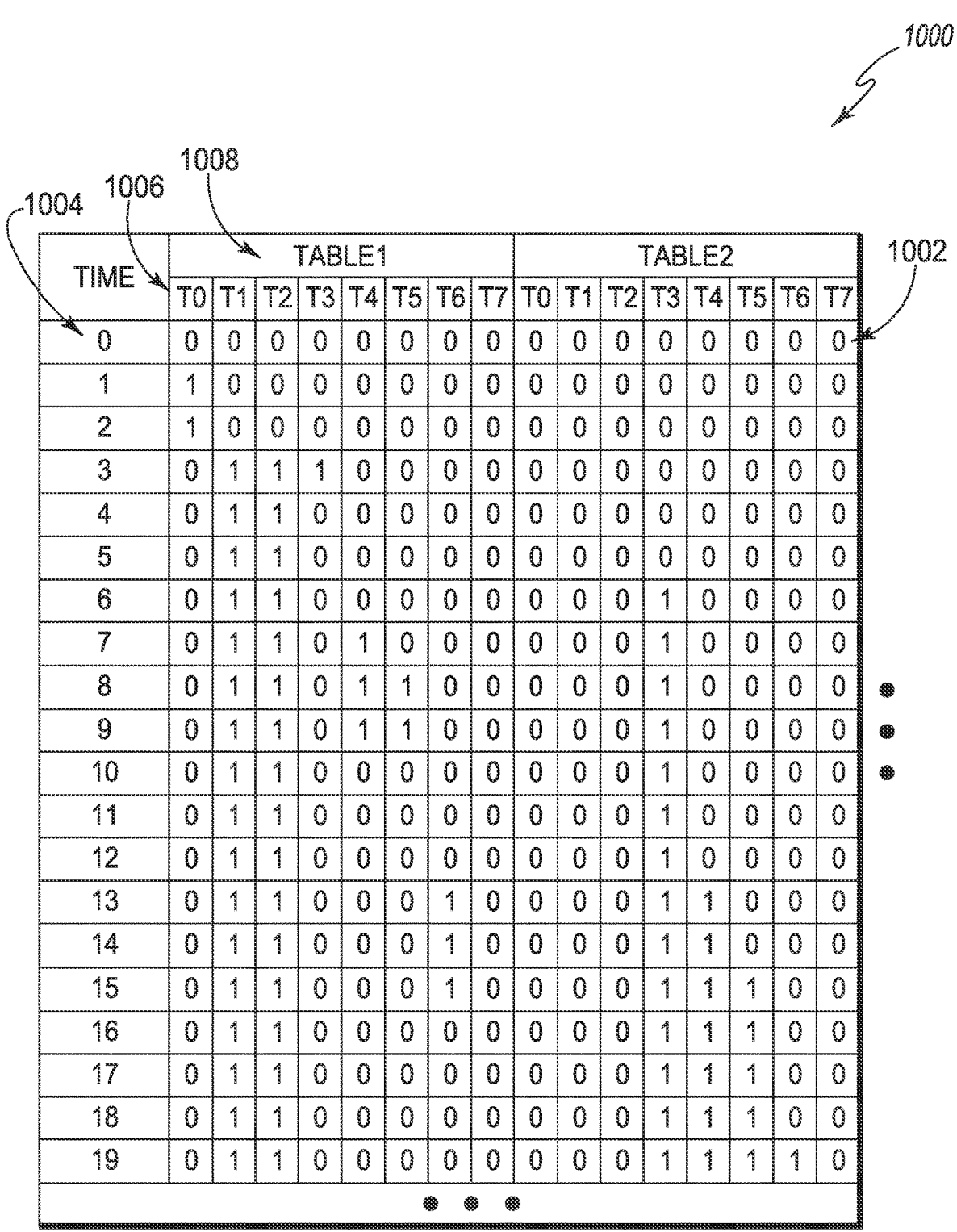
FIG. 10 is a schematic diagram illustrating exemplary recognition data that may be generated by the base station device of FIGS. 1-3.

In block 616, the base station device 102 transmits recognition data to the remote analytics server 106. The recognition data may be generated from image capture data received from multiple capture devices 104. Accordingly, the recognition data may include timestamps and, for each timestamp, a corresponding binary vector indicated recognized medical devices for each capture device 104. One potential embodiment of recognition data that may be transmitted to the analytics server 106 is illustrated in FIG. 10 and described further below. The recognition data may be transmitted wirelessly, by a wired connection, or otherwise transmitted to the analytics server 106. After transmitting the recognition data, the method 600 loops back to block 602, in which the base station device 102 may continue receiving image capture data from one or more capture devices 104.

Referring now to FIG. 7, in use, the analytics server 106 may execute a method 700 for analyzing recognition data. It should be appreciated that, in some embodiments, the operations of the method 700 may be performed by one or more components of the environment 340 of the analytics server 106 as shown in FIG. 3. The method 700 begins with block 702, in which the analytics server 106 receives recognition data from a base station device 102. As described above, the recognition data may include timestamps and, for each timestamp, a corresponding binary vector indicated recognized medical devices for one or more capture devices 104.

In block 704, the analytics server 106 generates medical device usage data based on the recognition data associated with all monitored locations in the operating room. In block 706, the analytics server 106 may coordinate recognition data based on timestamp. That is, the analytics server 106 may consider recognition data from all monitored locations for a particular timestamp. In block 708, the analytics server 106 infers location and/or use of the medical devices based on the recognition data. For example, the analytics server 106 may set a corresponding location for medical devices that are recognized at a particular capture device 104. As another example, the analytics server 106 may infer that a medical device is in use when it is no longer recognized at any capture device 104. One potential embodiment of a method for inferring the location and/or use of the medical devices 14 is illustrated in FIG. 8 and described further below. One potential embodiment of inferred usage data that may be generated by the analytics server 106 is illustrated in FIG. 11 and described further below.

In block 710, the analytics server 106 determines whether to analyze recognition data from additional base station devices 102. For example, the analytics server 106 may collect recognition data from base station devices 102 located at multiple different facilities (e.g., hospitals). If the analytics server 106 determines to analyze recognition data from additional base station devices 102, the method 700 loops back to block 702. If the analytics server 106 determines not to analyze recognition data from additional base station devices 102, the method 700 advances to block 712.

In block 712, the analytics server 106 analyzes medical device usage data across multiple surgical procedures, which may have been received from multiple base station devices 102 (e.g., from multiple hospitals or other facilities). The analytics server 106 may analyze, for example, which medical devices are used for particular procedures and in what order, among other data. Accordingly, the analytics server 106 may generate analytics data based on real-world usage data collected for the medical devices. Thus, the analytics data may be used to identify usage trends for medical devices that may be otherwise unavailable through other means, such as tracking medical device sales or surveying customers. Accordingly, the analytics data may be used to optimize medical device deployment, for example by more efficiently distributing, grouping, or otherwise packaging medical devices that are commonly used together.

In some embodiments, in block 714 the analytics server 106 may perform pattern recognition with the medical device usage data. For example, the analytics server 106 may identify typical medical device usage sequences or other patterns associated with particular medical device sequences. In some embodiments, in block 716 the analytics server 106 may perform anomaly detection with the medical device usage data. For example, the analytics server 106 may identify emerging modifications or alterations to surgical procedures as they are performed in the field. Continuing that example, the analytics server 106 may identify circumstances in which a surgical process diverges from a common usage sequence. As another example, the analytics server 106 may detect an excess delay at a particular step of a surgical process, which may indicate lack of timely availability of a medical device or a malfunctioning device.

Figure 12:
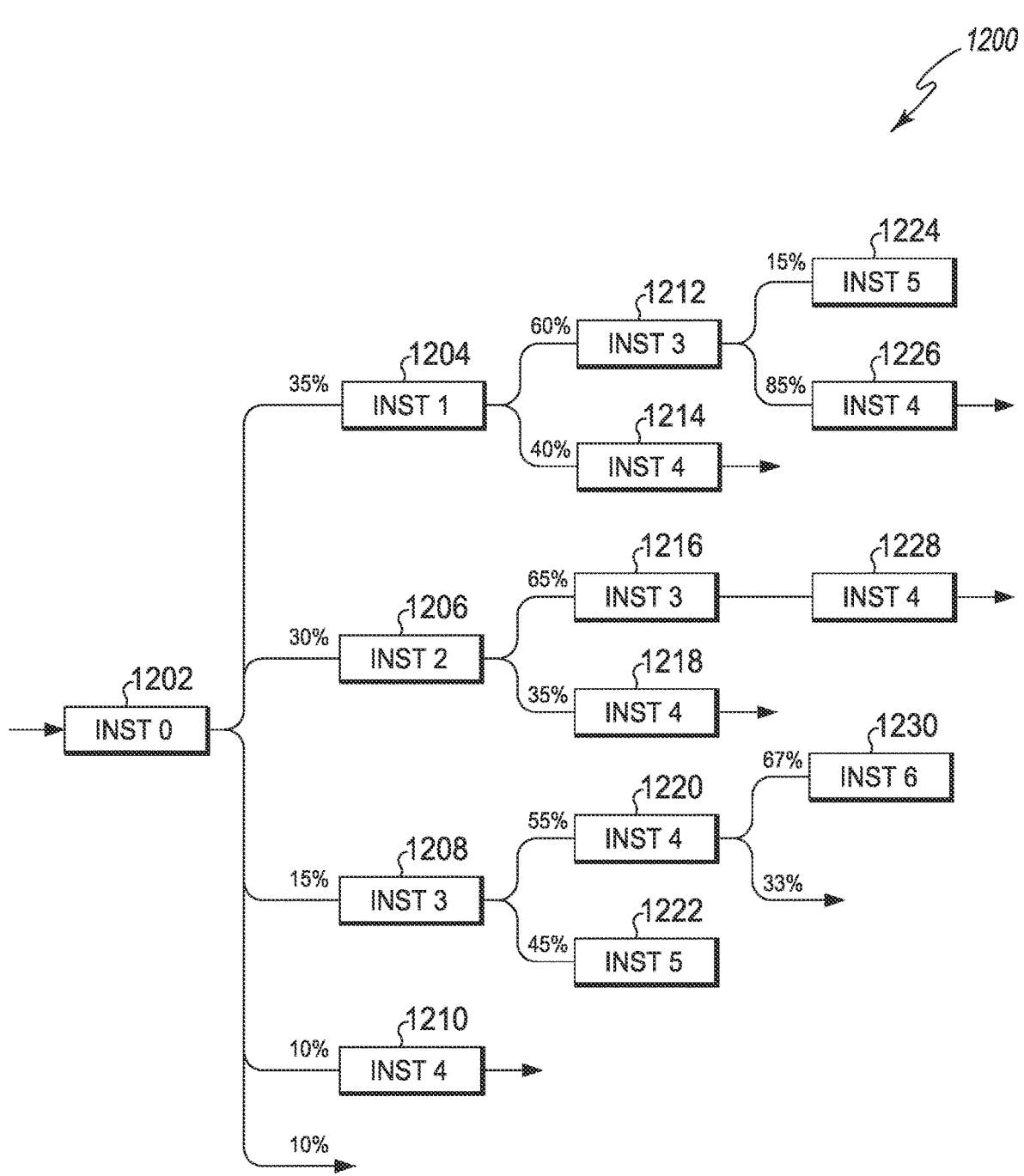
FIG. 12 is a schematic diagram illustrating exemplary medical device analytics data that may be generated by the analytics server of FIGS. 1-3.

In some embodiments, in block 718 the analytics server 106 determines a medical device sequence and relationship for a particular surgical procedure. For example, the analytics server 106 may identify the particular medical devices that are used in a surgical procedure as well as associated percentages of use for each medical device. In some embodiments, the analytics server 106 may determine the frequency with which a particular medical device is used in a procedure given that another medical device has been used. One potential embodiment of such analysis is illustrated in FIG. 12 and described further below.

In block 720, the analytics server 106 may provide access to analytical usage data generated based on the inferred medical device usage data. The analytical usage data may be provided to one or more client devices, for example, through a web site, portal, dashboard, native application, mobile application, application programming interface, or other interface of the analytics server 106. In some embodiments, the analytical usage data may be integrated with or otherwise incorporated in a common data layer used to analyze other data related to the medical devices (e.g., sales data or other business data). As described above, the analytical usage data may be used to improve efficiency, for example by optimizing trays or other sets of medical devices or otherwise improving efficiency. After providing the access, the method 700 loops back to block 702, in which the analytics server 106 may continue receiving recognition data from base station devices 102.

Referring now to FIG. 8, in use, the analytics server 106 may execute a method 800 for inferring medical device usage data. It should be appreciated that, in some embodiments, the operations of the method 800 may be performed by one or more components of the environment 340 of the analytics server 106 as shown in FIG. 3. In particular, the method 800 may be executed in connection with block 708 of FIG. 7, described above. Accordingly, the method 800 may be supplied with recognition data received from a base station device 102 for a particular timestamp. The method 800 begins with block 802, in which the analytics server 106 determines whether a medical device was recognized at any location within the recognition data. For example, the analytics server 106 may determine whether a bit in a bit vector associated with the medical device is set. In block 804, the analytics server 106 checks whether the medical device was recognized. If not, the method 800 branches ahead to block 810, described below. If a medical device was recognized, the method 800 advances to block 806.

In block 806, the analytics server 106 labels the medical device with the particular location at which it was recognized. The medical device may be labeled, for example, with a table number, name, or other identifier for a particular location within the operating room. As another example, the medical device may be labeled with a name or other identifier of an associated capture device 104, which may not require any knowledge of the particular configuration of the operating room. In some embodiments, in block 808 the medical device may be labeled with a device state. For example, for an instrument tray or an instrument case, the analytics server 106 may label the device as open or closed. To determine the state, the analytics server 106 may, for example, determine whether a bit in the bit vector for either state is set, and then assign a corresponding state label (e.g., TrayOpen, TrayClosed). After labeling the medical device, the method 800 branches to block 818, described below.

Referring back to block 804, if the medical device was not recognized, the method 800 branches to block 810, in which the analytics server 106 determines whether the medical device has been previously recognized at any location. For example, the analytics server 106 may determine whether the recognition data for previous timestamps includes any set bits for the medical device. As another example, the analytics server 106 may determine whether the medical device usage data for previous timestamps indicates that the medical device has been labeled at any location. In block 812, the analytics server 106 checks whether the medical device was previously recognized. If not, the method 800 branches ahead to block 816, described below. If the medical device was previously recognized, the method 800 advances to block 814.

In block 814, analytics server 106 labels the medical device as in use. In this circumstance, the medical device was previously recognized at one or more locations and is now no longer recognized at any location. Thus, the analytics server 106 may infer that the medical device is in use, for example at the operating table 12, in transit between monitored locations, or otherwise used in the operating room 10. After labeling the medical device, the method 800 branches to block 818, described below.

Referring back to block 812, if the medical device was not previously recognized, the method 800 branches to block 816, in which the medical device is labeled as not seen. In some embodiments, an medical device that is not seen may be labeled with a predetermined label (e.g., NotSeen), or may remain blank, null, uninitialized, or otherwise empty. Such medical devices that are not seen may not have been selected for use in the surgical procedure, may not have been placed on an entry table 16, may remain within a tray or case that is closed, or otherwise may not be in use. After labeling the medical device, the method 800 advances to block 818.

In block 818, the analytics server 106 determines whether to infer usage information for additional medical devices. The analytics server 106 may, for example, perform inference for each medical device that may be represented by the bit vector in the recognition data, for each medical device included in the medical device library 330, or otherwise perform recognition for a predetermined group of medical devices. If the analytics server 106 determines to infer usage information for additional medical devices, the method 800 loops back to block 802. If the analytics server 106 determines not to infer usage data for additional medical devices, the method 800 is completed. The analytics server 106 may use the inferred medical device usage data to generate additional analytics data as described above in connection with FIG. 7.

Referring now to FIG. 9, diagram 900 illustrates captured image data and medical device recognition that may be performed by the system 100. The diagram 900 shows images 902, 904, which represent image data captured by two capture devices 104. Illustratively, the images 902, 904 represent image data captured at the respective tables 16, 18 of FIG. 1. As shown, multiple medical devices 14 are visible in the captured images. Illustratively, image 902 shows a bearing inserter 906 positioned on the table 16. Image 902 also shows a tool tray 908 that is open and includes multiple additional medical devices 14, including shell trials, shell trial liners, surgical instruments, and other medical devices. Similarly, image 904 shows a straight impaction handle 910 positioned on the table 18.

The diagram 900 also shows the results of object recognition performed by the base station device 102 as overlay information. In particular, the overlay on the image 902 shows a bounding box 912, a label 914, and a confidence score 916 associated with the bearing inserter 906. The bounding box 912, the label 914, and the confidence score 916 correspond to output from the machine learning model 326, and indicate that the machine learning model 326 has recognized a particular medical device 14 identified by the label 914. As shown, the image 902 also includes additional bounding boxes, labels, and confidence scores generated for the tool tray 908 and other medical devices visible within the tool tray 908.

Similarly, the overlay on the image 904 shows a bounding box 918, a label 920, and a confidence score 922 associated with the straight impactor 910. The bounding box 918, the label 920, and the confidence score 922 correspond to output from the machine learning model 326, indicating that the machine learning model 326 has recognized a particular medical device 14 identified by the label 920.

As described above, the base station device 102 may use results from the machine learning model 326 to generate recognition data indicative of medical devices recognized in the monitored locations associated with the capture devices 104. Referring now to FIG. 10, diagram 1000 illustrates one potential embodiment of recognition data that may be generated by the base station device 102. As shown, the recognition data is illustratively an array of binary vectors 1002. Each binary vector 1002 is associated with a timestamp 1004, which may be embodied as a separate data field or an index in the recognition data. Although illustrated as sequential integers, in some embodiments the timestamps 1004 may be embodied as time values (e.g., a number of elapsed seconds or fractional seconds and/or a time of day value).

Each column 1006 of the binary vectors 1002 corresponds to a particular medical device 14 and/or to a particular label that may be output by the machine learning model 326, which are labeled as T0 through T7 in the diagram 1000. The columns 1006 are further organized into groups 1008. Each group 1008 corresponds to a monitored location associated with a capture device 104. Illustratively, the diagram 1000 includes two groups 1008 that are respectively associated with tables 16, 18 in the operating room 10 (labeled Table 1 and Table 2 in the diagram 1000). Although the illustrative diagram 1000 shows recognition data for eight medical devices and two monitored locations, it should be understood that in some embodiments, the recognition data may include information for any number of medical devices and/or monitored locations. For example, in some embodiments the recognition data may include information for many more medical devices 14 (e.g., potentially hundreds or thousands of medical devices included in the medical device library 330). Similarly, in some embodiments, the recognition data may include information for a single monitored location or information for three or more monitored locations.

In the illustrative embodiment shown in FIG. 10, a binary value of zero in a column 1006 indicates that the corresponding medical device 14 was not recognized in the monitored location, and a binary value of one indicates that the corresponding medical device 14 was recognized in the monitored location. For example, in the illustrative diagram 1000, medical device T0 was recognized at Table 1 at timestamp 1, and was no longer recognized after timestamp 2. As another example, medical device T3 was recognized at Table 1 at timestamp 3 and was also recognized at Table 2 at timestamp 6.

As described above, after generating the recognition data, the base station device 102 transmits the recognition data to the analytics server 106. The base station device 102 may transfer the recognition data in blocks (e.g., as a single upload for a particular procedure), may stream the recognition data continually, may compress the recognition data to reduce required bandwidth, or otherwise may transfer the recognition data to the analytics server 106. After transmitting the recognition data, the base station device 102 may not retain or otherwise store the recognition data.

As described above, after receiving the recognition data, the analytics server 106 generates usage data by performing inferences on the recognition data. Referring now to FIG. 11, diagram 1100 illustrates one potential embodiment of medical device usage data that may be generated by the analytics server 106. As shown, the medical device usage data is illustratively a table of labels or symbols 1102. Each row of labels 1102 is associated with a timestamp 1104, which correspond to the timestamps 1004 of the recognition data. Accordingly, each timestamp 1104 may be embodied as a separate data field or an index in the medical device usage data. Although illustrated as sequential integers, in some embodiments the timestamps may be embodied as time values (e.g., a number of elapsed seconds or fractional seconds and/or a time of day value).

The medical device usage data is further organized into columns 1106. Each column 1106 corresponds to a particular medical device 14, which are labeled Tool1 through Tool7 in the diagram 1100. The labels 1102 included in a column 1106 each may represent whether the corresponding medical device 14 has been recognized, in which monitored location the medical device 14 was recognized, whether the medical device 14 is in use, and, for some medical devices, a state of the device.

For example, in the illustrative embodiment, Tool1 may represent a tool tray similar to the tool tray 908 shown in FIG. 9. Initially, in timestamp 0, Tool1 is not recognized in any location and thus its entry in the medical device usage data is blank. At timestamp 1, Tool1 is recognized in the TrayClosed state. At timestamp 3, Tool1 is recognized in the TrayOpen state. The TrayClosed and TrayOpen states shown in FIG. 11 may be determined using multiple medical device columns in the recognition data. For example, in the illustrative recognition data shown in FIG. 10, the columns labeled T0 may correspond to the tray 908 in the TrayClosed state, and the columns labeled T1 may correspond to the tray 908 in the TrayOpen state. Continuing that example, the analytics server 106 may combine those columns T0, T1 to generate medical device usage data for Tool1 including device state data.

As another example, as shown in FIG. 11, Tool2 is recognized at Table 1 starting at timestamp 3, and Tool2 remains at Table 1 for the observed duration. Tool2 corresponds to the columns labeled T2 in FIG. 10. Illustratively, Tool2 may correspond to a trial liner or other medical device that is visible within the tray 908 when in the TrayOpen state as shown in FIG. 9, but that is not removed from the tray 908.

As yet another example, the medical device usage data indicates that at timestamp 3, Tool3 is located at Table 1, from timestamps 4-5, Tool3 is InUse, and from timestamp 6 on, Tool3 is located at Table1. Tool3 may correspond to a straight impaction handle as shown in FIG. 9 that is removed from the tray 908, used, and then placed on the table 18 as illustrated. Tool3 corresponds to the columns labeled T3 in FIG. 10. As shown in FIG. 10, T3 is first recognized in the column associated with Table 1 at timestamp 3. T3 is also recognized in the column associated with Table 2 starting at timestamp 6. T3 is not recognized in any column at timestamps 4-5. Accordingly, based on the recognition data, the analytics server 106 infers that the medical device Tool3 is in use during the timestamps 4-5.

As shown in FIG. 11, the analytics server 106 may make similar inferences of use for Tool4 through Tool6. As shown, multiple medical devices may be in use at the same time. Additionally, although not illustrated in FIG. 11, it should be understood that a medical device may be used at multiple different times during a procedure. Additionally, and as shown by Tool7, in some embodiments a medical device may not be recognized in any location, and thus the analytics server 106 may infer that this medical device is not used during the procedure. Further, although not illustrated in FIG. 11, in some embodiments the analytics server 106 may also determine a monitored location along with the medical device state for medical devices such as Tool1.

As described above, after generating the medical device usage data, the analytics server 106 may perform additional analysis, including analyzing medical device usage data collected from many base station devices 102 over the course of many surgical procedures. As an example analysis, the analytics server 106 may determine sequences of medical devices 14 that are used during surgical procedures as well as relative percentages or other frequency information for each medical device. Referring now to FIG. 12, diagram 1200 illustrates one potential embodiment of such analytics data that may be generated by the analytics server 106.

The diagram 1200 illustrates a decision tree structure that describes the relative frequency that particular medical devices 14 are used for a certain surgical procedure. During the execution of a surgical procedure such as a total hip replacement surgery, the orthopaedic surgeon may choose among many medical devices with which to perform each particular step of the procedure. Additionally, the particular medical device that is used may impact the selection of medical devices to be used at subsequent steps of the procedure. Accordingly, the decision tree shown in FIG. 12 represents potential sequences of medical devices that have been observed as being used as part of a surgical procedure, along with corresponding percentages. Each node in the decision tree represents a particular medical device. Each edge represents a medical device that may be used as the next medical device in a sequence. Each edge is labeled with the frequency that the particular medical device has been observed to be used.

For example, in an illustrative embodiment the diagram 1200 illustrates analytical data generated for part of a total hip replacement surgical procedure. Node 1202, labeled Inst 0, represents a surgical reamer having a particular size in millimeters (e.g., 40 mm). Node 1204, labeled Inst 1, represents a surgical reamer having a size one millimeter larger than the node 1202 (e.g., 41 mm). Node 1206, labeled Inst 2, represents a surgical reamer having a size two millimeters larger than the node 1202 (e.g., 42 mm). Node 1208, labeled Inst 3, represents a trial shell having a particular size (e.g. 40 mm). Node 1210, labeled Inst 4, represents a trial liner having a particular size (e.g., 40 mm). As shown, after starting at node 1202 with a given surgical reamer, in 35% of procedures, the surgeon next uses a reamer that is one millimeter larger (i.e., an odd increment), in 30% of procedures the surgeon next uses a reamer that is two millimeters larger (i.e., an even increment), in 15% of procedures, the surgeon next uses a trial shell, in 10% of procedures, the surgeon next uses a trial liner (i.e., without using a trial shell), and in 10% of procedures the surgeon next uses another medical device not shown in FIG. 12.

After selecting the medical device of node 1204, in 60% of procedures the surgeon next uses Inst 3 in node 1212 (e.g., a trial shell), and in 40% of procedures the surgeon next uses Inst 4 in node 1214 (e.g., a trial liner). After selecting the medical device of node 1212, in 15% of procedures the surgeon next proceeds to node 1224, which is labeled Inst 5 and which represents a trial shell having a different size (e.g., 42 mm). Additionally, after selecting the medical device of node 1212, in 85% of procedures the surgeon next uses Inst 4 in node 1226 (e.g., the 40 mm trial liner).

After selecting the medical device of node 1206, in 65% of procedures the surgeon next uses Inst 3 in node 1216 (e.g., a trial shell), and in 35% of procedures the surgeon next uses Inst 4 in node 1218 (e.g., a trial insert). Illustratively, after selecting the medical device of node 1216, in all procedures the surgeon next uses Inst 4 in node 1228 (e.g., a trial insert).

After selecting the medical device of node 1208, in 55% of procedures the surgeon next uses Inst 4 in node 1220 (e.g., a trial insert), and in 45% of procedures the surgeon next uses Inst 5 in node 1222 (e.g., a larger trial shell). After selecting the medical device of node 1222, in 67% of procedures the surgeon next proceeds to node 1230, which is labeled Inst 6 and which represents a trial liner having a different size (e.g., 42 mm). After selecting the medical device of node 1222, in 33% of procedures the surgeon next selects a different medical device, not shown in FIG. 12.

Of course, the sequence of medical devices and associated percentages shown in FIG. 12 are merely illustrative. In other embodiments, the analytics server 106 may generate similar decision tree structures for other surgical procedures and/or for other medical devices.

Using this detailed information on the sequence of medical devices and associated frequencies, the analytics server 106 may generate additional analytics data. For example, the analytics server 106 may analyze medical device usage data to determine frequencies for particular combinations of medical devices or other surgical workflows. The analytics server 106 may also filter or otherwise process the medical device usage data based on additional related data, such as facility size, geographic location, or other information.

Figure 13:
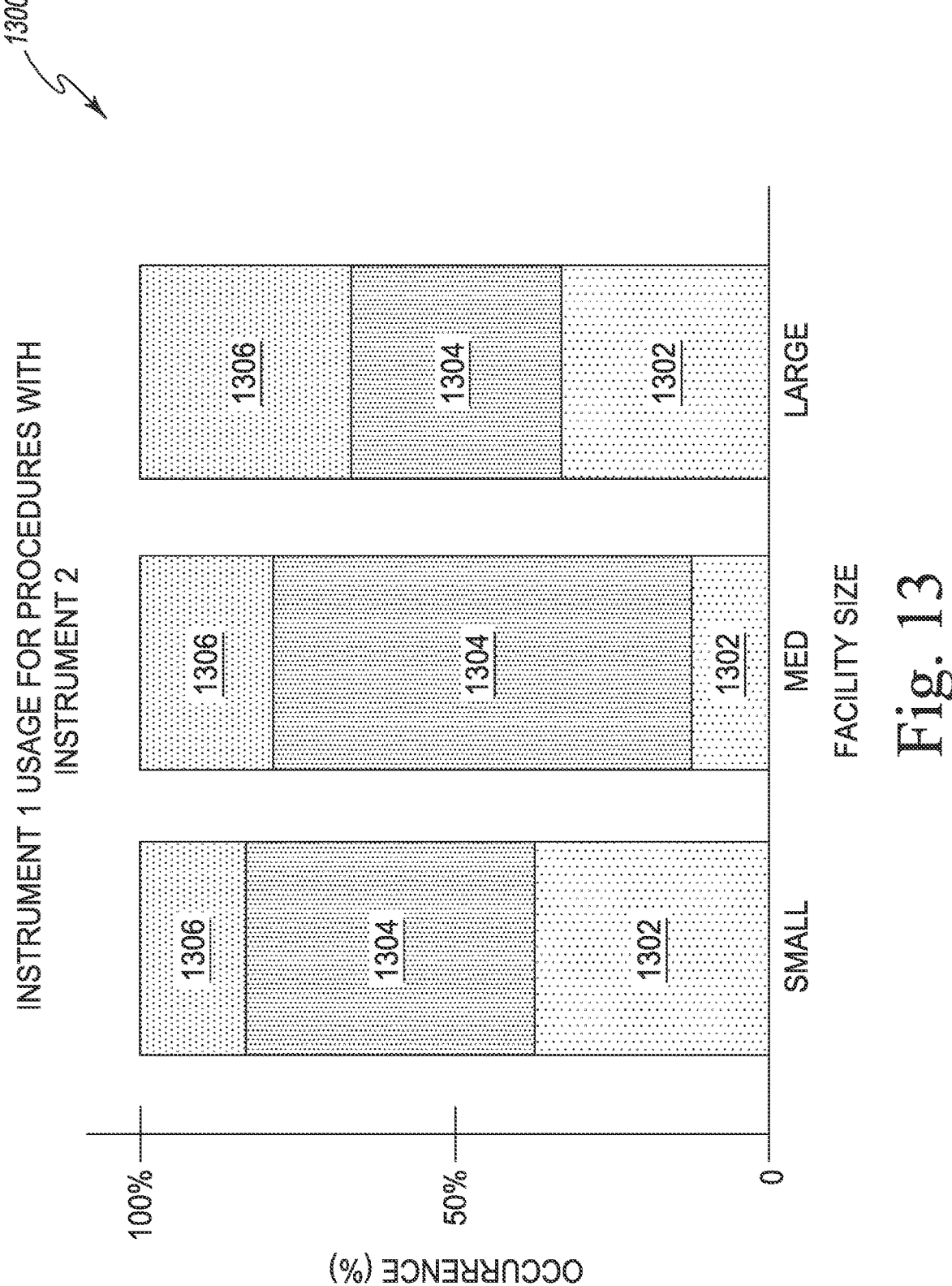
FIGS. 13 and 14 are bar charts illustrating exemplary medical device analytics data that may be generated by the analytics server of FIGS. 1-3.

Referring now to FIG. 13, chart 1300 illustrates one potential analysis that may be performed by the analytics server 106. The illustrative chart 1300 categorizes surgical reamer usage for hip replacement procedures that include the use of a trial shell. The chart 1300 further categorizes procedures by facility size. Bar 1302 represents procedures that use a single reamer (e.g., Inst 0 in FIG. 12). Bar 1304 represents procedures that use multiple reamers with 1 mm size increments (e.g., Inst 0 and Inst 1 in FIG. 12). Bar 1306 represents procedures that use multiple reamers with 2 mm size increments (e.g., Inst 0 and Inst 2 in FIG. 12). As shown, each of small, medium, and large size facilities may have different patterns of usage for surgical reamers in procedures that include the use of a trial shell.

Figure 14:
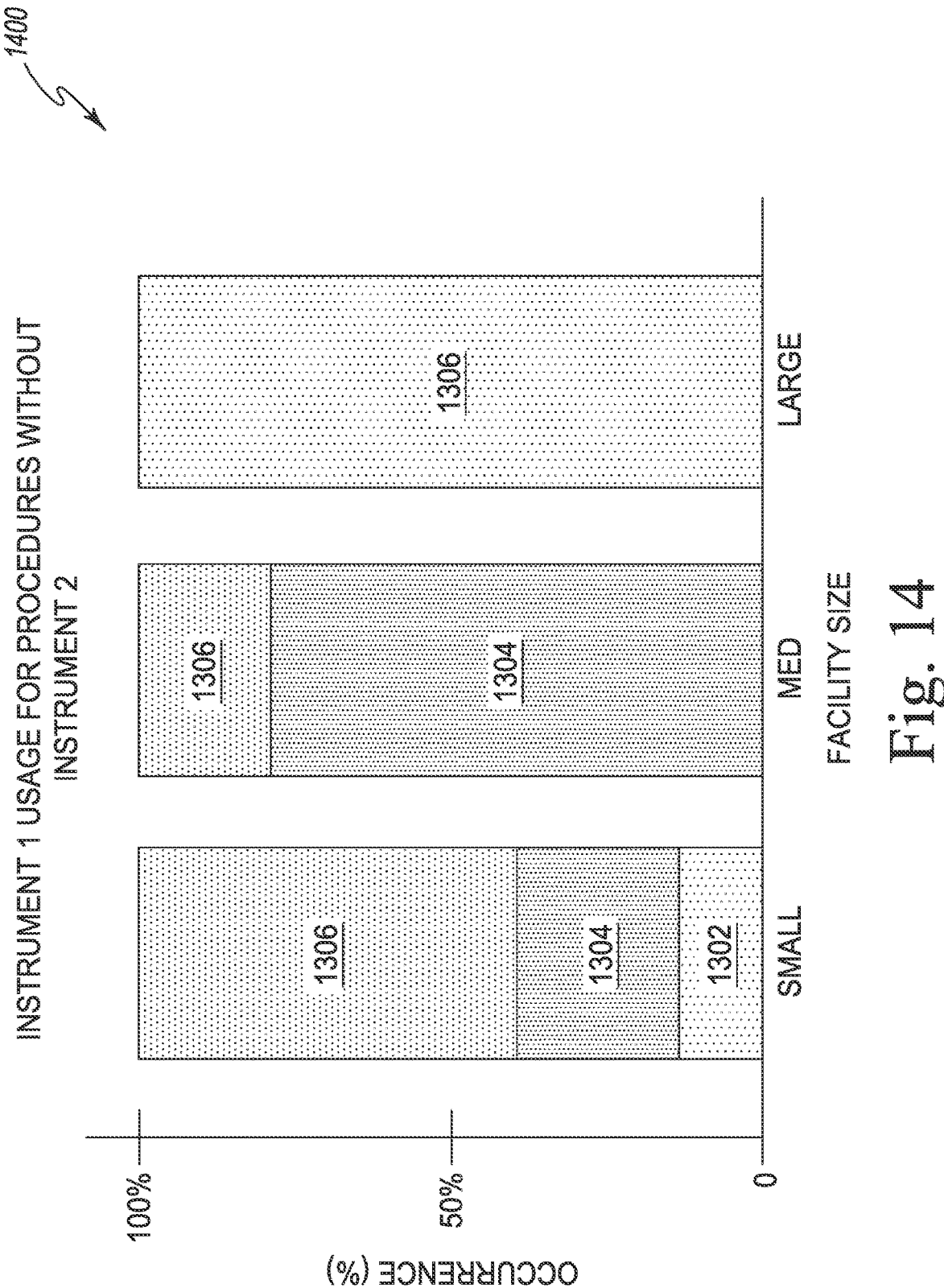

Referring now to FIG. 14, chart 1400 illustrates another potential analysis that may be performed by the analytics server 106. The illustrative chart 1400 categorizes surgical reamer usage for hip replacement procedures that do not include the use of a trial shell. Similar to the chart 1300, the chart 1400 includes the bar 1302 representing procedures using a single reamer, the bar 1304 representing procedures using reamers with a 1 mm increment, and the bar 1306 representing procedures using reamers with a 2 mm increment. As shown, each of the small, medium, and large facility sizes have different proportions of reamer usage. Additionally, the proportions of reamer usage are different between procedures without a trial shell shown in FIG. 14 as compared to the proportions for procedures with a trial shell as shown in FIG. 13. Analytics data such as that shown in FIGS. 13 and 14 may be used to select medical devices 14 for use in a surgical procedure, which may improve efficiency. Additionally, FIGS. 13 and 14 are illustrative of certain types of analytics data that may be generated from the medical device usage data. It should be understood that the analytics server 106 may provide additional analysis of the medical device usage data based on medical device sequencing and frequency of use. The analytics server 106 may make such analytics data available to one or more client devices, for example through a web portal or a mobile application.

Figure 15:
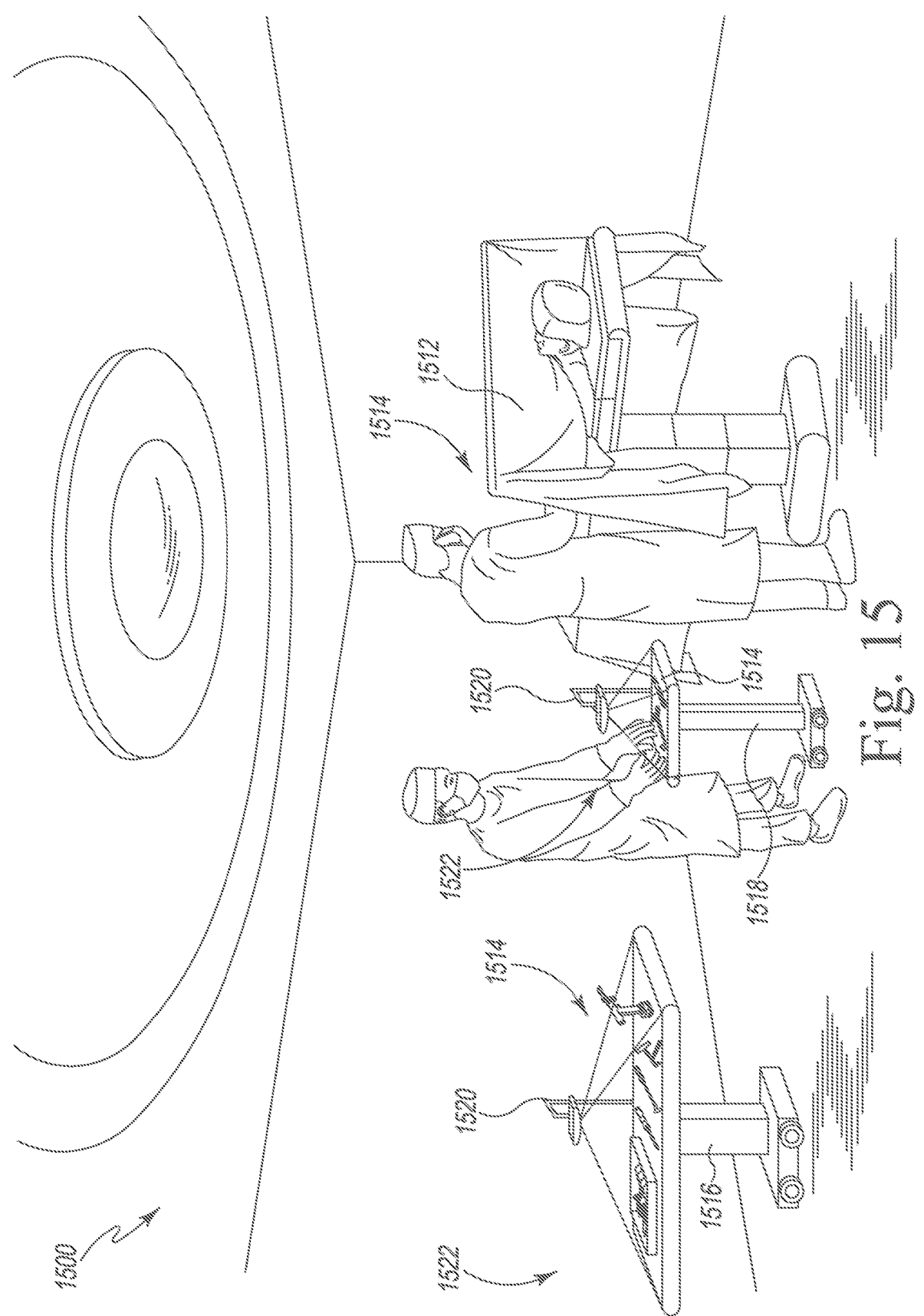
FIG. 15 is a schematic diagram of another embodiment of a system for medical device usage tracking installed in an operating room.

Referring now to FIG. 15, another illustrative operating room 1500 is shown. The operating room 1500 is similar to the operating room 10 shown in FIG. 1 and includes similar fixtures and components. For example, the operating room 1500 includes an operating table 1512 as well as other tables 1516, 1518. Medical devices 1514 may be stored, staged, or otherwise arranged at the tables 1516, 1518, and may be used by the surgeon or other user.

As shown, the operating room 1500 includes multiple capture devices 1520, which each may be embodied as a capture device 104. Unlike the capture devices 20 shown in FIG. 1, which are fixed in the operating room 10, each of the capture devices 1520 is attached to a respective table 1516, 1518. A field of view 1522 of each capture device 1520 is directed toward the respective table 1516, 1518. Accordingly, each table 1516, 1518 is a monitored location within the operating room 1500. Usage of the medical devices 1514 may be tracked by the system 100 as described above.

It should be appreciated that the system 100 as described herein may be used to track and analyze usage of various medical devices, including but not limited to surgical instruments, such as orthopaedic surgical instruments used in an orthopaedic surgical procedure. Similarly, although described as being used in connection with an operating room 10, it should be understood that the system 100 may be used outside of the operating room 10 within the hospital or other site of care. For example, the system 100 may be used to track medical devices during sterile processing at the hospital or site of care. Additionally or alternatively, in some embodiments the system 100 may be used to monitor medical devices in environments other than the site of care. For example, the system 100 may track medical devices through inventory, manufacturing, and other nodes of a commercial supply chain.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A system for medical device usage monitoring, the system comprising a capture device, a base station device, and an analytics server, wherein:

the capture device comprises a camera device and a capture engine to (i) capture image capture data, wherein the image capture data is indicative of a time series of images representing a monitored location of an operating room, and (ii) transmit the image capture data to the base station device;

the base station device comprises: (i) a capture interface to receive the image capture data from the image capture device; (ii) a recognition engine to recognize a medical device in the image capture data with a machine learning model to generate recognition data, wherein to recognize the medical device comprises to determine whether any medical device of a predetermined library of medical devices is represented in the image capture data, wherein the recognition data is indicative of whether the medical device is represented at the monitored location at a corresponding time in the image capture data, wherein the recognition data comprises a binary vector, and wherein each bit of the binary vector corresponds to a medical device of the predetermined library of medical devices; and (iii) an analytics interface to transmit the recognition data to the analytics server; and the analytics server comprises: (i) a recognition interface to receive the recognition data from the base station device; and (ii) an inference engine to generate medical device usage data based on the recognition data, wherein the medical device usage data is indicative of a usage label associated with the medical device for each corresponding time of the recognition data, wherein the usage label is indicative an in-use status when the medical device is not represented at the monitored location at the corresponding time and was represented at the monitored location at a first time earlier than the corresponding time.

2. The system of claim 1, wherein to recognize the medical device comprises to identify a type of the medical device and a size of the medical device.

3. The system of claim 2, wherein the type of the medical device comprises a surgical reamer, a shell inserter, a shell trial, or a trial liner.

4. The system of claim 1, wherein:

the capture interface is further to receive second image capture data from a second image capture device, wherein the second image capture data is indicative of a time series of images representing a second monitored location of the operating room; and the recognition engine is further to recognize the medical device in the second image capture data with the machine learning model to generate the recognition data, wherein the recognition data is further indicative of whether the medical device is represented at a corresponding time in the second image capture data.

5. The system of claim 1, wherein the usage label is indicative of the monitored location or the in-use status.

6. The system of claim 5, wherein to generate the medical device usage data comprises, for each corresponding time of the recognition data, to:

determine whether the recognition data indicates that the medical device is represented at the monitored location;

generate the usage label indicative of the monitored location in response to a determination that the recognition data indicates that the medical device is represented at the monitored location; and generate the usage label indicative of the in-use status in response to a determination that the recognition data indicates that the medical device was represented at the monitored location at the first time earlier than the corresponding time and is not represented at the monitored location at the corresponding time.

7. The system of claim 5, wherein:

the recognition data is further indicative of whether the medical device is represented at a second monitored location at the corresponding time; and to generate the medical device usage data comprises, for each corresponding time of the recognition data, to:

determine whether the recognition data indicates that the medical device is represented at any corresponding monitored location of the monitored location and the second monitored location;

generate the usage label indicative of the corresponding monitored location in response to a determination that the recognition data indicates that the medical device is represented at any corresponding monitored location; and generate the usage label indicative of the in-use status in response to a determination that the recognition data indicates that the medical device was represented at any corresponding monitored location at a time earlier than the corresponding time and is not represented at any corresponding monitored location at the corresponding time.

8. The system of claim 1, wherein the analytics server further comprises an analytics engine to analyze the medical device usage data to generate analytical usage data.

9. The system of claim 8, wherein:

the recognition interface is further to receive recognition data from a second computing device; and to generate the medical device usage data comprises to generate the medical device usage data based on the recognition data received from the computing device and the recognition data received from the second computing device.

10. The system of claim 8, wherein to analyze the medical device usage data comprises to determine a medical device sequence and a frequency based on the medical device usage data.

11. The system of claim 8, wherein the analytics server further comprises an analytics portal interface to expose the analytical usage data to a client device.

* * * * *